(12) United States Patent
Charvin et al.

(10) Patent No.: US 10,442,818 B2
(45) Date of Patent: *Oct. 15, 2019

(54) CHROMONE OXIME DERIVATIVE AND ITS USE AS ALLOSTERIC MODULATOR OF METABOTROPIC GLUTAMATE RECEPTORS

(71) Applicant: Prexton Therapeutics SA, Geneva (CH)

(72) Inventors: Delphine Charvin, Gex (FR); Baptiste Manteau, Lingolsheim (FR); Vincent Pomel, Groisy (FR); François Conquet, Beaument (FR)

(73) Assignee: Prexton Therapeutics SA, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/000,338

(22) Filed: Jun. 5, 2018

(65) Prior Publication Data
US 2018/0291034 A1 Oct. 11, 2018

Related U.S. Application Data

(63) Continuation of application No. 15/506,941, filed as application No. PCT/EP2015/069601 on Aug. 27, 2015, now Pat. No. 10,017,521.

(30) Foreign Application Priority Data

Aug. 27, 2014 (EP) ...................................... 14182468

(51) Int. Cl.
*A61K 31/5377* (2006.01)
*C07D 495/04* (2006.01)

(52) U.S. Cl.
CPC ........ C07D 495/04 (2013.01); A61K 31/5377 (2013.01)

(58) Field of Classification Search
CPC .......................... A61K 31/5377; C07D 495/04
USPC ........................................ 514/233.8; 544/127
See application file for complete search history.

(56) References Cited

U.S. PATENT DOCUMENTS

| | | | |
|---|---|---|---|
| 4,065,467 A | 12/1977 | Doria et al. | |
| 4,777,252 A | 10/1988 | Slusarchyk et al. | |
| 10,017,521 B2 * | 7/2018 | Charvin | A61K 31/5377 |
| 2003/0109574 A1 | 6/2003 | Komata et al. | |
| 2004/0198750 A1 | 10/2004 | Green et al. | |
| 2017/0253613 A1 | 9/2017 | Charvin et al. | |
| 2018/0271874 A1 | 9/2018 | Charvin et al. | |

FOREIGN PATENT DOCUMENTS

| EP | 0 787 723 A1 | 8/1997 |
|---|---|---|
| RU | 2 557 059 C2 | 7/2015 |
| WO | WO 2004/052869 A1 | 6/2004 |
| WO | WO 2004/092154 A2 | 10/2004 |
| WO | WO 2007/011701 A1 | 1/2007 |
| WO | WO 2009/010454 A2 | 1/2009 |
| WO | WO 2009/010455 A2 | 1/2009 |
| WO | WO 2011/051478 A1 | 5/2011 |
| WO | WO 2011/069063 A2 | 6/2011 |
| WO | WO 2017/032874 A1 | 3/2017 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Extended European Search Report for Application No. 14182468.0 dated Nov. 3, 2014.
International Search Report and Written Opinion for Application No. PCT/EP2015/069601 dated Nov. 18, 2015.
International Search Report and Written Opinion for Application No. PCT/EP2016/070175 dated Oct. 27, 2016.
International Search Report and Written Opinion for Application No. PCT/EP2010/066537 dated Feb. 11, 2011.
[No Author Listed] European Medicines Agency: STALEVO— Annex I: Summary of product characteristics; Annex II: A. Manufacturer responsible for batch release, B. Conditions or restrictions regarding supply and use, C. Other conditions and requirements of the marketing authorisation, D. Conditions or restrictions with regard to the safe and effective use of the medicinal product; Annex III: Labelling and Package Leaflet. Oct. 2008. 160 pages.
[No Author Listed] Editorial: Dopa decarboxylase inhibitors. Br Med J 1974;4:250-1.

(Continued)

*Primary Examiner* — Jeffrey H Murray
(74) *Attorney, Agent, or Firm* — Wolf, Greenfield & Sacks, P.C.

(57) ABSTRACT

The present invention provides a novel chromone oxime derivative of formula (I), which is a modulator of nervous system receptors sensitive to glutamate and, furthermore, presents an advantageously high brain penetration upon oral administration. The invention also relates to a pharmaceutical composition containing this compound, and to its use for the treatment or prevention of conditions associated with altered glutamatergic signalling and/or functions, or conditions which can be affected by alteration of glutamate level or signalling, particularly acute and chronic neurological and/or psychiatric disorders.

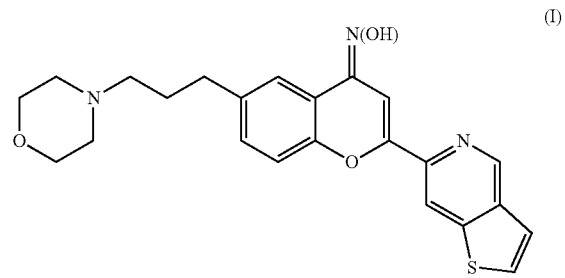

(I)

5 Claims, 10 Drawing Sheets

(56) References Cited

OTHER PUBLICATIONS

Figure 1:
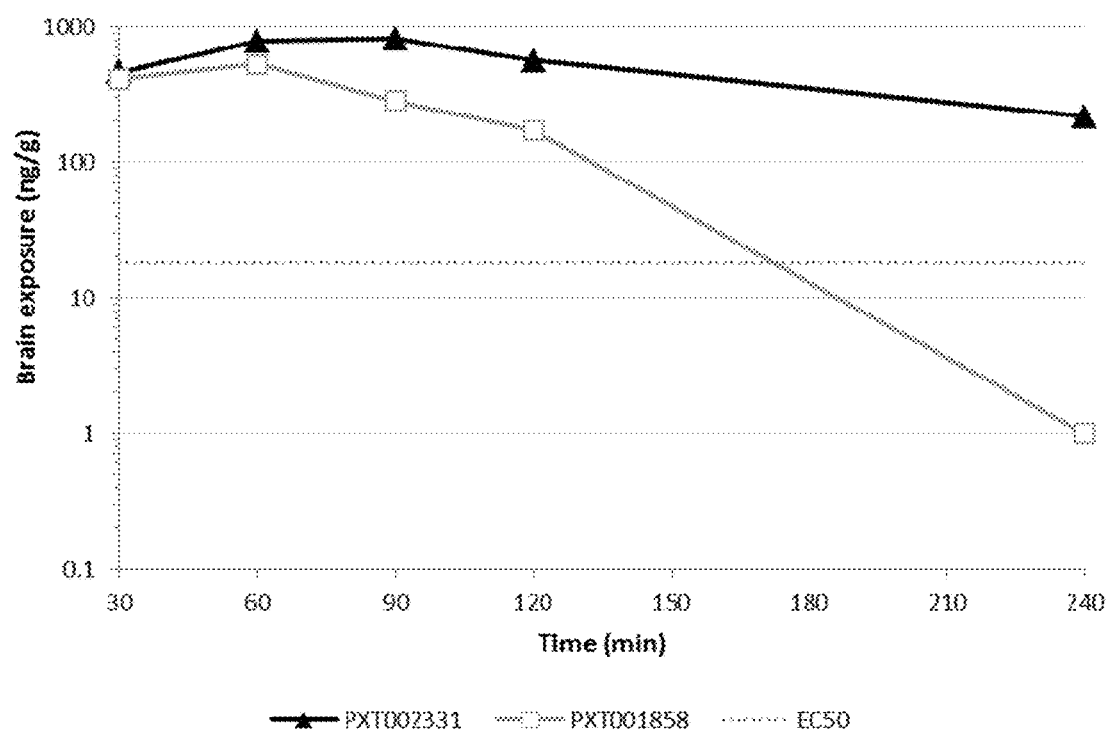

Ares et al., A convenient large-scale synthesis of 5-Methoxyflavone and its application to analog preparation. J. Org. Chem. 1993;68:7903-7905.

Battaglia et al., Pharmacological activation of mGlu4 metabotropic glutamate receptors reduces nigrostriatal degeneration in mice treated with 1-methyl-4-phenyl-1,2,3,6-tetrahydropyridine. J. Neurosci. Jul. 5, 2006;26(27):7222-9.

Becker et al., Autistic-like syndrome in mu opioid receptor null mice is relieved by facilitated mGluR4 activity. Neuropsychopharmacology. Aug. 2014;39(9):2049-60. doi: 10.1038/npp.2014.59. Epub Mar. 12, 2014.

Bennouar et al., Synergy between L-DOPA and a novel positive allosteric modulator of metabotropic glutamate receptor 4: implications for Parkinson's disease treatment and dyskinesia. Neuropharmacology. Mar. 2013;66:158-69. doi: 0.1016/j.neuropharm.2012.03.022. Epub Apr. 3, 2012.

Boldyrev et al., Homocysteine and its derivatives as possible modulators of neuronal and non-neuronal cell glutamate receptors in Alzheimer's disease. J Alzheimers Dis. May 2007;11(2):219-28.

Bräuner-Osborne et al., Ligands for glutamate receptors: design and therapeutic prospects. J Med Chem. Jul. 13, 2000;43(14):2609-45.

Bridges et al., G-protein-coupled receptors: from classical modes of modulation to allosteric mechanisms. ACS Chem Biol. Sep. 19, 2008;3(9):530-41. doi: 10.1021/cb800116f. Epub Jul. 25, 2008.

Broekkamp et al., Major tranquillizers basis can be distinguished from minor tranquillizers on the basis of effects on marble burying and swim-induced grooming in mice. Eur J Pharmacol. Jul. 31, 1986;126(3):223-9.

Brotchie et al., Levodopa-induced dyskinesia in Parkinson's disease. J Neural Transm (Vienna). Mar. 2005;112(3):359-91. Epub Dec. 22, 2004.

Bruno et al., Metabotropic glutamate receptor subtypes as targets for neuroprotective drugs. J Cereb Blood Flow Metab. Sep. 2001;21(9):1013-33.

Bundgaard, Chapter 1: Design of prodrugs: Bioreversible derivatives for various functional groups and chemical entities. In: Design of Prodrugs, Elsevier, Amsterdam 1985. pp. 7-9 and 21-24.

Chang et al., Metabotropic glutamate receptor 4 expression in colorectal carcinoma and its prognostic significance. Clin Cancer Res. May 1, 2005;11(9):3288-95.

Chiocchetti et al., Glutamatergic candidate genes in autism spectrum disorder: an overview. J Neural Transm (Vienna). Sep. 2014;121(9):1081-106. doi: 10.1007/s00702-014-1161-y. Epub Feb. 4, 2014.

Conn et al., Activation of metabotropic glutamate receptors as a novel approach for the treatment of schizophrenia. Trends Pharmacol Sci. Jan. 2009;30(1):25-31. doi: 10.1016/j.tips.2008.10.006. Epub Dec. 6, 2008.

Conn et al., Metabotropic glutamate receptors in the basal ganglia motor circuit. Nat Rev Neurosci. Oct. 2005;6(10):787-98.

Conn et al., Pharmacology and functions of metabotropic glutamate receptors. Annu Rev Pharmacol Toxicol. 1997;37:205-37.

Constantino et al, 1-Benzopyran-4-one antioxidants as aldose reductase inhibitors. J Med Chem. Jun. 3, 1999;42(11):1881-93.

Cryan et al., Antidepressant and anxiolytic-like effects in mice lacking the group III metabotropic glutamate receptor mGluR7. Eur J Neurosci. Jun. 2003;17(11):2409-17.

Del Sorbo et al., Levodopa-induced dyskinesias and their management. J Neurol. Aug. 2008;255 Suppl 4:32-41. doi: 10.1007/s00415-008-4006-5.

Di Stefano et al., Antiparkinson prodrugs. Molecules. Jan. 16, 2008;13(1):46-68.

Di Stefano et al., L-Dopa prodrugs: an overview of trends for improving Parkinson's disease treatment. Curr Pharm Des. 2011;17(32):3482-93.

Engers et al., Synthesis and evaluation of a series of heterobiarylamides that are centrally penetrant metabotropic glutamate receptor 4 (mGluR4) positive allosteric modulators (PAMs). J Med Chem. Jul. 23, 2009;52(14):4115-8. doi: 10.1021/jm9005065.

Eschle et al., Behavioral comparison of sucrose and 1-2-amino-4-phosphonobutyrate (L-AP4) tastes in rats: does L-AP4 have a sweet taste? Neuroscience. Aug. 13, 2008;155(2):522-9. doi: 10.1016/j.neuroscience.2008.06.006. Epub Jun. 8, 2008.

Fahn, The spectrum of levodopa-induced dyskinesias. Ann Neurol. Apr. 2000;47(4 Suppl 1):S2-9; discussion S9-11.

Ferreira et al., Synthesis of 13-substituted alanines via Michael addition of nucleophiles to dehydroalanine derivatives. J. Chem. Soc., Perkin Trans. 2000;1:3317-3324.

Flor et al., Molecular cloning, functional expression and pharmacological characterization of the human metabotropic glutamate receptor type 4. Neuropharmacology. Feb. 1995;34(2):149-55.

Goudet et al., Group III metabotropic glutamate receptors inhibit hyperalgesia in animal models of inflammation and neuropathic pain. Pain. Jul. 2008;137(1):112-24. Epub Sep. 27, 2007.

Hansson et al., An in vitro selected binding protein (affibody) shows conformation-dependent recognition of the respiratory syncytial virus (RSV) G protein. Immunotechnology. Mar. 1999;4(3-4):237-52.

Hauser, IPX066: a novel carbidopa-levodopa extended-release formulation. Expert Rev Neurother. Feb. 2012;12(2):133-40. doi: 10.1586/ern.11.195.

Henning et al., Genetic modification of adenovirus 5 tropism by a novel class of ligands based on a three-helix bundle scaffold derived from staphylococcal protein A. Hum Gene Ther. Aug. 10, 2002;13(12):1427-39.

Iacovelli et al., Pharmacological activation of mGlu4 metabotropic glutamate receptors inhibits the growth of medulloblastomas. J Neurosci. Aug. 9, 2006;26(32):8388-97.

Karaman, Computational-aided design for dopamine prodrugs based on novel chemical approach. Chem Biol Drug Des. Nov. 2011;78(5):853-63. doi: 10.1111/j.1747-0285.2011.01208.x. Epub Sep. 26, 2011.

Klak et al., Combined administration of PHCCC, a positive allosteric modulator of mGlu4 receptors and ACPT-I, mGlu III receptor agonist evokes antidepressant-like effects in rats. Amino Acids. Feb, 2007;32(2):169-72. Epub Aug. 2, 2006.

Konieczny et al., LY354740, a group II metabotropic glutamate receptor agonist with potential antiparkinsonian properties in rats. Naunyn Schmiedebergs Arch Pharmacol. Oct. 1998;358(4):500-2.

Lopez et al., Functional interaction between adenosine A2A and group III metabotropic glutamate receptors to reduce parkinsonian symptoms in rats. Neuropharmacology. Sep. 2008;55(4):483-90. doi: 10.1016/j.neuropharm.2008.06.038. Epub Jun. 27, 2008.

Maj et al., (+)-PHCCC, a positive allosteric modulator of mGluR4: characterization, mechanism of action, and neuroprotection. Neuropharmacology. Dec. 2003;45(7):895-906.

Makoff et al., Molecular characterization and localization of human metabotropic glutamate receptor type 4. Brain Res Mol Brain Res. Apr. 1996;37(1-2):239-48.

Marino et al., Allosteric modulation of group III metabotropic glutamate receptor 4: a potential approach to Parkinson's disease treatment. Proc Natl Acad Sci U S A. Nov. 11, 2003;100(23):13668-73. Epub Oct. 30, 2003.

Mathiesen et al., Positive allosteric modulation of the human metabotropic glutamate receptor 4 (hmGluR4) by SIB-1893 and MPEP. Br J Pharmacol. Mar. 2003;138(6):1026-30.

Mattson, Excitotoxic and excitoprotective mechanisms: abundant targets for the prevention and treatment of neurodegenerative disorders. Neuromolecular Med. 2003;3(2):65-94.

Meli et al., Activation of mGlu1 but not mGlu5 metabotropic glutamate receptors contributes to postischemic neuronal injury in vitro and in vivo. Pharmacol Biochem Behav. Sep. 2002;73(2):439-46.

Menichincheri et al., Catecholic flavonoids acting as telomerase inhibitors. J Med Chem. Dec. 16, 2004;47(26):6466-75.

Narayanan et al., Multivariate genetic determinants of EEG oscillations in schizophrenia and psychotic bipolar disorder from the BSNIP study. Transl Psychiatry. Jun. 23, 2015;5:e588. doi: 10.1038/tp.2015.76.

Niswender et al., Discovery, characterization, and antiparkinsonian effect of novel positive allosteric modulators of metabotropic glu-

(56) References Cited

OTHER PUBLICATIONS tamate receptor 4. Mol Pharmacol. Nov. 2008;74(5):1345-58. doi: 10.1124/mol.108.049551. Epub Jul. 29, 2008.
Niswender et al., Positive allosteric modulators of the metabotropic glutamate receptor subtype 4 (mGluR4): Part I. Discovery of pyrazolo[3,4-d]pyrimidines as novel mGluR4 positive allosteric modulators. Bioorg Med Chem Lett. Oct. 15, 2008;18(20):5626-30. doi: 10.1016/j.bmcl.2008.08.087. Epub Aug. 29, 2008.
Nurnberger et al., Identification of pathways for bipolar disorder: a meta-analysis. JAMA Psychiatry. Jun. 2014;71(6):657-64. doi: 10.1001/jamapsychiatry.2014.176.
Obeso et al., The evolution and origin of motor complications in Parkinson's disease. Neurology. 2000;55(11 Suppl 4):S13-20; discussion S21-3.
Palucha et al., Group III mGlu receptor agonists produce anxiolytic- and antidepressant-like effects after central administration in rats. Neuropharmacology. Feb. 2004;46(2):151-9.
Palucha et al., Metabotropic glutamate receptor ligands as possible anxiolytic and antidepressant drugs. Pharmacol Ther. Jul. 2007;115(1):116-47. Epub May 13, 2007.
Palucha-Poniewiera et al., Peripheral administration of group III mGlu receptor agonist ACPT-1 exerts potential antipsychotic effects in rodents. Neuropharmacology. Sep. 2008;55(4):517-24. doi: 10.1016/j.neuropharm.2008.06.033. Epub Jun. 27, 2008.
Pessimissis et al., The glutamatergic system expression in human PC-3 and LNCaP prostate cancer cells. Anticancer Res. Jan. 2009;29(1):371-7.
Pilc et al., Multiple MPEP administrations evoke anxiolytic- and antidepressant-like effects in rats. Neuropharmacology. Aug. 2002;43(2):181-7.
Pin et al., The metabotropic glutamate receptors: structure, activation mechanism and pharmacology. Curr Drug Targets CNS Neurol Disord. Jun. 2002;1(3):297-317.
Pires et al., Acute effects of selective serotonin reuptake inhibitors on neuroleptic-induced catalepsy in mice. Braz J Med Biol Res. Dec. 2005;38(12):1867-72. Epub Nov. 9, 2005.
Rascol et al., New treatments for levodopa-induced motor complications. Mov Disord. Sep. 15, 2015;30(11):1451-60. doi: 10.1002/mds.26362. Epub Aug. 21, 2015.
Schoepp et al., Pharmacological agents acting at subtypes of metabotropic glutamate receptors. Neuropharmacology. Oct. 1999;38(10):1431-76.
Seeberger et al., Levodopa/carbidopa/entacapone in Parkinson's disease. Expert Rev Neurother. Jul. 2009;9(7):929-40. doi: 10.1586/ern.09.64.
Shiozaki et al., Actions of adenosine A2A receptor antagonist KW-6002 on drug-induced catalepsy and hypokinesia caused by reserpine or MPTP. Psychopharmacology (Berl). Nov. 1999; 147(1):90-5.
Soto et al., Glutamate receptor mutations in psychiatric and neurodevelopmental disorders. Commun Integr Biol. Jan. 1, 2014;7(1):e27887. doi: 10.4161/cib.27887. Epub Feb. 6, 2014.
Stachowicz et al., Anxiolytic-like effects of PHCCC, an allosteric modulator of mGlu4 receptors, in rats. Eur J Pharmacol. Sep. 13, 2004;498(1-3):153-6.
Stephans et al., Methamphetamine-induced neurotoxicity: roles for glutamate and dopamine efflux. Synapse. Jul. 1994;17(3):203-9.
Taki et al., Emission ratiometric imaging of intracellular zinc: design of a benzoxazole fluorescent sensor and its application in two-photon microscopy. J Am Chem Soc. Jan. 28, 2004;126(3):712-3.
Tambasco et al., Clinical aspects and management of levodopa-induced dyskinesia. Parkinsons Dis. 2012;2012:745947. doi: 10.1155/2012/745947. Epub Jun. 3, 2012.
Tanabe et al., A family of metabotropic glutamate receptors. Neuron. Jan. 1992;8(1):169-79.
Thanvi et al., Levodopa-induced dyskinesia in Parkinson's disease: clinical features, pathogenesis, prevention and treatment. Postgrad Med J. Jun. 2007;83(980):384-8.
Uehara et al., Metabotropic glutamate receptor type 4 is involved in autoinhibitory cascade for glucagon secretion by alpha-cells of islet of Langerhans. Diabetes. Ap. 2004;53(4):998-1006.
Vernon et al., Additive neuroprotection by metabotropic glutamate receptor subtype-selective ligands in a rat Parkinson's model. Neuroreport. Mar. 5, 2008;19(4):475-8. doi: 10.1097/WNR. 0b013e3282f602df.
Vernon et al., Selective activation of group III metabotropic glutamate receptors by L-(+)-2-amino-4-phosphonobutryic acid protects the nigrostriatal system against 6-hydroxydopamine toxicity in vivo. J Pharmacol Exp Ther. Jan. 2007;320(1):397-409. Epub Sep. 29, 2006.
Williams et al., Neuroprotective and symptomatic effects of targeting group III mGlu receptors in neurodegenerative disease. J Neurochem. Apr. 2014;129(1):4-20. doi: 10.1111/jnc.12608. Epub Dec. 2, 2013.
Williams et al., Positive allosteric modulators of the metabotropic glutamate receptor subtype 4 (mGluR4). Part II: Challenges in hit-to-lead. Bioorg Med Chem Lett. Feb. 1, 2009;19(3):962-6. doi: 10.1016/j.bmcl.2008.11.104. Epub Dec. 25, 2008.
Wu et al., Group III human metabotropic glutamate receptors 4, 7 and 8: molecular cloning, functional expression, and comparison of pharmacological properties in RGT cells. Brain Res Mol Brain Res. Jan. 1998;53(1-2):88-97.
Zhang et al., Effects of activation of group III metabotropic glutamate receptors on spinal synaptic transmission in a rat model of neuropathic pain. Neuroscience. Jan. 23, 2009;158(2):875-84. doi: 10.1016/j.neuroscience.2008.10.042. Epub Oct. 30, 2008.

* cited by examiner

CHROMONE OXIME DERIVATIVE AND ITS USE AS ALLOSTERIC MODULATOR OF METABOTROPIC GLUTAMATE RECEPTORS

This application is a continuation of U.S. application Ser. No. 15/506,941, filed Feb. 27, 2017, which is a national phase application under 35 U.S.C. § 371 of International Application No. PCT/EP2015/069601, filed Aug. 27, 2015, which claims benefit of European Application No. 14182468.0, filed Aug. 27, 2014, the entire contents of each of which are hereby incorporated by reference.

The present invention provides a novel chromone oxime derivative which is a modulator of nervous system receptors sensitive to the neuroexcitatory amino acid glutamate and, furthermore, presents an advantageously high brain exposure upon oral administration. These properties make the chromone oxime derivative according to the invention particularly suitable as a medicament, e.g., in the treatment or prevention of acute and chronic neurological and/or psychiatric disorders.

It is known that glutamate is involved in numerous nervous functions. Important roles are therefore attributed to glutamatergic receptors, in particular as regards the conduction of nerve impulse, synaptic plasticity, the development of the nervous system, learning and memory.

Glutamate is also the main endogenous neurotoxin, being responsible for the neuronal death observed after ischemia, hypoxia, epileptic fits or traumatisms of the brain. Therefore glutamate receptors are clearly considered to be involved in various disorders of the nervous system and neurodegenerative diseases.

The glutamatergic system includes glutamate receptors and transporters as well as enzymes of glutamate metabolism. Two main types of glutamatergic receptors have been characterized: ionotropic (iGluRs) and metabotropic (mGluRs) receptors. Ionotropic glutamate receptors have been identified based on their pharmacology and subsequently through molecular biology. The iGluR family includes the NMDA (N-methyl-D-aspartate), AMPA (alpha-amino-3-hydroxy-5-methyl-4-isoxazole propionic acid) and the kainate receptor subfamilies, so named for the chemical agonist that selectively binds to the subfamily members. iGluRs are voltage-gated ion channels that allow cation influx upon glutamate binding. They are directly responsible for the generation of action potentials, they initiate neuroplastic changes in the CNS and are responsible for many diseases, including chronic pain. Metabotropic glutamate receptors are a family of seven transmembrane domain G-protein-coupled receptors (GPCR). So far, eight mGluR subtypes have been identified (mGluR1-mGluR8) and classified into three groups (I-III) based upon sequence homology, transduction mechanism and pharmacological profile. mGluRs belong to family 3 of the GPCR superfamily, and as such, they are characterized by a large extracellular amino terminal domain (ATD) where the glutamate binding site is located. mGluRs are localized throughout the nervous system (central and peripheral) and have been shown to play a role in homeostasis in many organ systems. They have been found to play an important role in particular in the induction of the long-term potentiation (LTP) and the long-term depression (LTD) of synaptic transmission, in the regulation of baroceptive reflexes, spatial learning, motor learning, postural and kinetic integration, and are considered to be involved in acute or chronic degenerative diseases such as Parkinson's disease, levodopa-induced dyskinesia, Alzheimer's disease, Amyotrophic Lateral Sclerosis, spinocerebellar ataxia, epilepsy or Huntington's disease, as well as neuropsychiatric disorders such as anxiety, depression, autism spectrum disorder, post-traumatic stress disorder and schizophrenia.

Thus, it has been clearly demonstrated that glutamatergic pathways are involved in the physiopathology of a number of neuronal damages and injuries. Many nervous system disorders including epilepsy and chronic or acute degenerative processes such as for example Alzheimer's disease, Huntington's disease, Parkinson's disease and Amyotrophic Lateral Sclerosis (Mattson M P., *Neuromolecular Med.*, 3(2), 65-94, 2003), but also AIDS-induced dementia, multiple sclerosis, spinal muscular atrophy, retinopathy, stroke, ischemia, hypoxia, hypoglycaemia and various traumatic brain injuries, involve neuronal cell death caused by imbalanced levels of glutamate. It has also been shown that drug-induced neurotoxicity, for example neurotoxic effects of methamphetamine (METH) on striatal dopaminergic neurons, could actually be mediated by over-stimulation of the glutamate receptors (Stephans S E and Yamamoto B K, *Synapse* 17(3), 203-9, 1994). Antidepressant and anxiolytic-like effects of compounds acting on glutamate have also been observed on mice, suggesting that glutamatergic transmission is implicated in the pathophysiology of affective disorders such as major depression, schizophrenia and anxiety (Palucha A et al., *Pharmacol. Ther.* 115(1), 116-47, 2007; Cryan J F et al., *Eur. J. Neurosc.* 17(11), 2409-17, 2003; Conn P J et al., *Trends Pharmacol. Sci.* 30(1), 25-31, 2009). Consequently, any compound able to modulate glutamatergic signalling or function would constitute a promising therapeutic compound for many disorders of the nervous system.

Moreover, compounds modulating glutamate level or signalling may be of great therapeutic value for diseases and/or disorders not directly mediated by glutamate levels and/or glutamate receptors malfunctioning, but which could be affected by alteration of glutamate levels or signaling.

The amino acid L-glutamate (referred to herein simply as glutamate) is the major excitatory neurotransmitter in the mammalian central and peripheral nervous system (CNS and PNS, respectively). It participates in all functions of the nervous system and affects nervous system development at all stages, from neuron migration, differentiation and death to the formation and elimination of synapses. Glutamate is ubiquitously distributed at high concentrations in the nervous system and is involved in virtually all physiological functions, such as learning and memory, motor control, development of synaptic plasticity, sensory perception, vision, respiration and regulation of cardiovascular function (Meldrum, 2000). Abnormalities in the glutamatergic system are known to incur neurotoxicity and other deleterious effects on neurotransmission, neuroenergetics, and cell viability. Accordingly, a considerable number of studies have been conducted to investigate the potential association between the glutamatergic system and neurological or psychiatric disorders.

Glutamate operates through two classes of receptors (Brauner-Osborne H et al., *J. Med. Chem.* 43(14), 2609-45, 2000). The first class of glutamate receptors is directly coupled to the opening of cation channels in the cellular membrane of the neurons. Therefore they are called ionotropic glutamate receptors (iGluRs). The iGluRs are divided into three subtypes, which are named according to their selective agonists: N-methyl-D-aspartate (NMDA), α-amino-3-hydroxy-5-methyl-4-isoxazole-propionic acid (AMPA), and kainate (KA). The second class of glutamate receptors consists of G-protein-coupled receptors (GPCRs)

called metabotropic glutamate receptors (mGluRs). These mGluRs are localized both pre- and post-synaptically. They are coupled to multiple second messenger systems and their role is to regulate the activity of the ionic channels or enzymes producing second messengers via G-proteins binding the GTP (Conn P J and Pin J P., *Annu. Rev. Pharmacol. Toxicol.*, 37, 205-37, 1997). Although they are generally not directly involved in rapid synaptic transmission, the mGluRs modulate the efficacy of the synapses by regulating either the post-synaptic channels and their receptors, or the pre-synaptic release or recapture of glutamate. Therefore, mGluRs play an important role in a variety of physiological processes such as long-term potentiation (LTP) and long-term depression (LTD) of synaptic transmission, regulation of baroreceptive reflexes, spatial learning, motor learning, and postural and kinetic integration.

To date, eight mGluRs have been cloned and classified in three groups according to their sequence homologies, pharmacological properties and signal transduction mechanisms. Group I includes mGluR1 and mGluR5, group II mGluR2 and mGluR3 and group III mGluR4, mGluR6, mGluR7 and mGluR8 (Pin J P and Acher F., *Curr. Drug Targets CNS Neurol. Disord.*, 1(3), 297-317, 2002; Schoepp D D et al., *Neuropharmacology*, 38(10), 1431-76, 1999).

mGluR ligands/modulators can be classified in two families depending on their site of interaction with the receptor (see Brauner-Osborne H et al., *J. Med. Chem.* 43(14), 2609-45, 2000 for review). The first family consists in orthosteric ligands (or competitive ligands) able to interact with the glutamate binding-site of the mGluRs, which is localized in the large extra-cellular N-terminal part of the receptor (about 560 amino acids). Examples of orthosteric ligands are S-DHPG or LY-367385 for group I mGluRs, LY-354740 or (2R-4R)-APDC for group II mGluRs and ACPT-I or L-AP4 for group III mGluRs. The second family of mGluRs ligands consists in allosteric ligands/modulators that interact with a different site from the extracellular active site of the receptor (see Bridges T M et al., *ACS Chem Biol,* 3(9), 530-41, 2008 for review). Their action results in a modulation of the effects induced by the endogenous ligand glutamate. Examples of such allosteric modulators are Ro-674853, MPEP or JNJ16259685 for group I mGluRs and CBiPES, LY181837 or LY487379 for group II mGluRs.

Examples of allosteric modulators were described for the mGluR subtype 4 (mGluR4). PHCCC, MPEP and SIB1893 (Maj M et al., *Neuropharmacology*, 45(7), 895-903, 2003; Mathiesen J M et al., *Br. J. Pharmacol.* 138(6), 1026-30, 2003) were the first ones described in 2003. More recently, more potent positive allosteric modulators were reported in the literature (Niswender C M et al., *Mol. Pharmacol.* 74(5), 1345-58, 2008; Niswender C M et al., *Bioorg. Med. Chem. Lett.* 18(20), 5626-30, 2008; Williams R et al., *Bioorg. Med. Chem. Lett.* 19(3), 962-6, 2009; Engers D W et al., *J. Med. Chem.* May 27 2009) and in two patent publications describing families of amido and heteroaromatic compounds (WO 2009/010454 and WO 2009/010455).

Numerous studies have already described the potential applications of mGluR modulators in neuroprotection (see Bruno V et al., *J. Cereb. Blood Flow Metab.*, 21(9), 1013-33, 2001 for review). For instance, antagonist compounds of group I mGluRs showed interesting results in animal models for anxiety and post-ischemic neuronal injury (Pilc A et al., *Neuropharmacology*, 43(2), 181-7, 2002; Meli E et al., *Pharmacol. Biochem. Behav.*, 73(2), 439-46, 2002), agonists of group II mGluRs showed good results in animal models for Parkinson and anxiety (Konieczny J et al., *Naunyn-Schmiederbergs Arch. Pharmacol.*, 358(4), 500-2, 1998).

Group III mGluR modulators showed positive results in several animal models of schizophrenia (Palucha-Poniewiera A et al., *Neuropharmacology*, 55(4), 517-24, 2008) and chronic pain (Goudet C et al., *Pain,* 137(1), 112-24, 2008; Zhang H M et al., *Neuroscience,* 158(2), 875-84, 2009).

Group III mGluR were also shown to exert the excitotoxic actions of homocysteine and homocysteic acid contributing to the neuronal pathology and immunosenescence that occur in Alzheimer Disease (Boldyrev A A and Johnson P, *J. Alzheimers Dis.* 11(2), 219-28, 2007). Moreover, group III mGluR modulators showed promising results in animal models of Parkinson's disease and neurodegeneration (Conn P J et al., *Nat. Rev. Neuroscience*, 6(10), 787-98, 2005 for review; Vernon A C et al., *J. Pharmacol. Exp. Ther.*, 320(1), 397-409, 2007; Lopez S et al., *Neuropharmacology*, 55(4), 483-90, 2008; Vernon A C et al., *Neuroreport*, 19(4), 475-8, 2008; Williams C J et al., *J. Neurochem.*, 129(1), 4-20, 2014 for review). It was further demonstrated with selective ligands that the mGluR subtype involved in these antiparkinsonian and neuroprotective effects was mGluR4 (Marino M J et al., *Proc. Natl. Acad. Sci. USA* 100(23), 13668-73, 2003; Battaglia G et al., *J. Neurosci.* 26(27), 7222-9, 2006; Niswender C M et al., Mol. *Pharmacol.* 74(5), 1345-58, 2008).

mGluR4 modulators were also shown to exert anxiolytic activity (Stachowicz K et al., *Eur. J. Pharmacol.*, 498(1-3), 153-6, 2004) and anti-depressive actions (Palucha A et al., *Neuropharmacology* 46(2), 151-9, 2004; Klak K et al., *Amino Acids* 32(2), 169-72, 2006).

In addition, mGluR4 were also shown to be involved in glucagon secretion inhibition (Uehara S., *Diabetes* 53(4), 998-1006, 2004). Therefore, orthosteric or positive allosteric modulators of mGluR4 have potential for the treatment of type 2 diabetes through its hypoglycemic effect.

Moreover, mGluR4 was shown to be expressed in prostate cancer cell-line (Pessimissis N et al., *Anticancer Res.* 29(1), 371-7, 2009) or colorectal carcinoma (Chang H J et al., *Cli. Cancer Res.* 11(9), 3288-95, 2005) and its activation with PHCCC was shown to inhibit growth of medulloblastomas (Iacovelli L et al., *J. Neurosci.* 26(32) 8388-97, 2006). mGluR4 modulators may therefore have also potential role for the treatment of cancers.

Finally, receptors of the umami taste expressed in taste tissues were shown to be variants of the mGluR4 receptor (Eschle B K., *Neuroscience,* 155(2), 522-9, 2008). As a consequence, mGluR4 modulators may also be useful as taste agents, flavour agents, flavour enhancing agents or food additives.

Chromone-derived core structures for pharmaceutically active compounds were described in the patent application WO 2004/092154. In the latter application, they are disclosed as inhibitors of protein kinases.

EP-A-0 787 723 relates to specific cyclopropachromen-carboxylic acid derivatives which are said to have mGluR antagonistic activity.

A new class of ligands of metabotropic glutamate receptors is described in WO 2011/051478. The chromone oxime derivatives provided in this document are highly potent modulators of mGluRs, particularly positive allosteric modulators of mGluR4, and can advantageously be used as pharmaceuticals, in particular in the treatment or prevention of acute and chronic neurological and/or psychiatric disorders.

In the context of the present invention, it has surprisingly been found that a novel chromone oxime derivative from the class of compounds described in WO 2011/051478 does not only show potent activity as a positive allosteric modulator of mGluRs but also has highly advantageous pharmacokinetic properties. In particular, this novel compound of formula (I) as shown below has been found to exhibit an improved brain exposure after oral administration as compared to the compounds taught in WO 2011/051478. The present invention thus solves the problem of providing a novel potent modulator of mGluRs, particularly a positive allosteric modulator of mGluR4, that has improved pharmacokinetic properties and, in particular, improved brain penetration.

The present invention thus relates to a compound of the following formula (I):

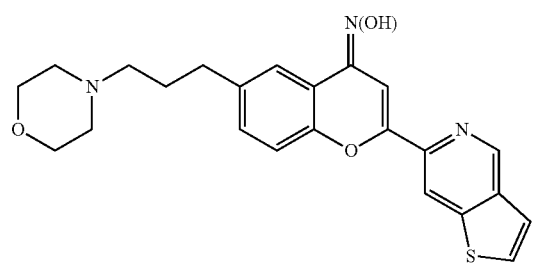

(I)

or a pharmaceutically acceptable salt, solvate or prodrug thereof. The compound of formula (I) is also referred to as "PXT002331" in this specification.

Accordingly, the invention relates to the compound 6-(3-morpholin-4-yl-propyl)-2-(thieno[3,2-c]pyridin-6-yl)-4H-chromen-4-one oxime or a pharmaceutically acceptable salt, solvate or prodrug thereof.

The compound of formula (I) according to the present invention has been found to substantially retain the potent therapeutic activity of the structurally related compound according to Example 127 of WO 2011/051478 while, unexpectedly, showing considerably improved pharmacokinetic properties and, in particular, a greatly improved brain exposure, as also demonstrated in Example 2.

Compound of formula (I)

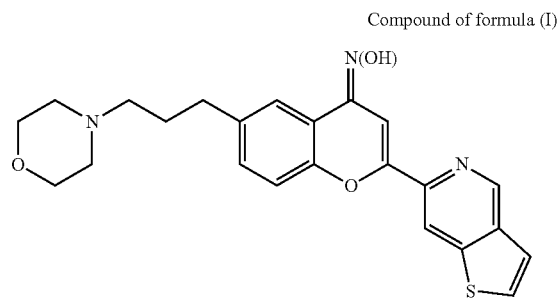

("PXT002331")
Potency on mGluR4: $pEC_{50} = 7.12$
Brain $AUC_{(o\text{-}inf)}$ (h*ng/g) $_{(10\ mg/kg\ p.o.)} = 2713$
Brain/plasma ratio $_{(T=1.5\ h)} = 6.5$ Example 127 of WO 2011/051478

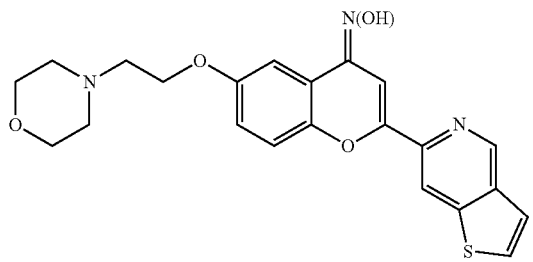

("PXT001858")
Potency on mGluR4: $pEC_{50} = 7.44$
Brain $AUC_{(o\text{-}inf)}$ (h*ng/g) $_{(10\ mg/kg\ p.o.)} = 838$
Brain/plasma ratio $_{(T=1.5\ h)} = 2.0$ These improved pharmacokinetic properties render the compound of formula (I) highly advantageous as a pharmaceutical, particularly as a brain penetrant pharmaceutical, e.g., for the medical intervention in neurological and/or psychiatric disorders. In accordance with this advantageous pharmacokinetic profile, the compound of formula (I) has further been demonstrated to show potent anti-parkinsonian efficacy in an MPTP-macaque model of Parkinson's disease, particularly at doses lower than or equal to 25 mg/kg by oral administration, as detailed in Example 3.

In accordance with the present invention, the compound of formula (I) is useful as a brain penetrant modulator of mGluRs of the nervous system. In particular, the compound of formula (I) is useful as a brain penetrant allosteric modulator of the mGluRs and can most advantageously be used as a brain penetrant positive allosteric modulator of mGluR4.

The present invention also relates to a pharmaceutical composition comprising the compound of formula (I) or a pharmaceutically acceptable salt, solvate or prodrug thereof in combination with a pharmaceutically acceptable excipient. Accordingly, the invention relates to the compound of formula (I) or a pharmaceutically acceptable salt, solvate or prodrug thereof for use as a medicament.

The present invention further relates to the compound of formula (I) or a pharmaceutically acceptable salt, solvate or prodrug thereof, or a pharmaceutical composition comprising any of the aforementioned entities in combination with a pharmaceutically acceptable excipient, for use in the treatment or prevention of a condition associated with altered glutamatergic signalling and/or functions, or a condition which can be affected by alteration of glutamate level or signalling. The use of the compound of formula (I) or a pharmaceutically acceptable salt, solvate or prodrug thereof for the preparation of a medicament for the treatment or prevention of a condition associated with altered glutamatergic signalling and/or functions, or a condition which can be affected by alteration of glutamate level or signalling is also within the scope of the invention.

Moreover, the invention relates to a method of treating or preventing a condition associated with altered glutamatergic signalling and/or functions, or a condition which can be affected by alteration of glutamate level or signalling in a mammal. Accordingly, the invention provides a method of treating or preventing a condition associated with altered glutamatergic signalling and/or functions, or a condition which can be affected by alteration of glutamate level or signalling, the method comprising the administration of the compound of formula (I) or a pharmaceutically acceptable salt, solvate or prodrug thereof, or a pharmaceutical composition comprising any of the aforementioned entities in combination with a pharmaceutically acceptable excipient, to a subject in need thereof (preferably a mammal, and more preferably a human).

The conditions associated with altered glutamatergic signalling and/or functions, or conditions which can be affected by alteration of glutamate level or signalling, which can be treated and/or prevented with the compound or the pharmaceutical composition according to the invention, include for example: epilepsy, including newborn, infantile, childhood and adult syndromes, partial (localization-related) and generalized epilepsies, with partial and generalized, convulsive and non-convulsive seizures, with and without impairment of consciousness, and status epilepticus; dementias and related diseases, including dementias of the Alzheimer's type (DAT), Alzheimer's disease, Pick's disease, vascular dementias, Lewy-body disease, dementias due to metabolic, toxic and deficiency diseases (including alcoholism, hypothyroidism, and vitamin B12 deficiency), AIDS-dementia complex, Creutzfeld-Jacob disease and atypical subacute spongiform encephalopathy; parkinsonism and movement disorders, including Parkinson's disease, multiple system atrophy, progressive supranuclear palsy, corticobasal degeneration, hepatolenticular degeneration, chorea (including Huntington's disease and hemiballismus), athetosis, dystonias (including spasmodic torticollis, occupational movement disorder, Gilles de la Tourette syndrome), tardive or drug induced dyskinesias (including levodopa-induced dyskinesia), tremor and myoclonus; motor neuron disease or amyotrophic lateral sclerosis (ALS); other neurodegenerative and/or hereditary disorders of the nervous system, including spinocerebrellar degenerations such as Friedrich's ataxia and other hereditary cerebellar ataxias, predominantly spinal muscular atrophies, hereditary neuropathies, and phakomatoses; disorders of the peripheral nervous system, including trigeminal neuralgia, facial nerve disorders, disorders of the other cranial nerves, nerve root and plexus disorders, mononeuritis such as carpal tunnel syndrome and sciatica, hereditary and idiopathic peripheral neuropathies, inflammatory and toxic neuropathies; multiple sclerosis and other demyelinating diseases of the nervous system; infantile cerebral palsy (spastic), monoplegic, paraplegic or tetraplegic; hemiplegia and hemiparesis, flaccid or spastic, and other paralytic syndromes; cerebrovascular disorders, including subarachnoid hemorrhage, intracerebral hemorrhage, occlusion and stenosis of precerebral arteries, occlusion of cerebral arteries including thrombosis and embolism, brain ischemia, stroke, transient ischemic attacks, atherosclerosis, cerebrovascular dementias, aneurysms, cerebral deficits due to cardiac bypass surgery and grafting; autism spectrum disorders, including autism, Asperger syndrome, childhood disintegrative disorder, and Rett syndrome; migraine, including classical migraine and variants such as cluster headache; headache; myoneural disorders including myasthenia gravis, acute muscle spasms, myopathies including muscular dystrophies, mytotonias and familial periodic paralysis; disorders of the eye and visual pathways, including retinal disorders, and visual disturbances; intracranial trauma/injury and their sequels; trauma/injury to nerves and spinal cord and their sequels; poisoning and toxic effects of nonmedicinal substances; accidental poisoning by drugs, medicinal substances and biologicals acting on the central, peripheral and autonomic system; neurological and psychiatric adverse effects of drugs, medicinal and biological substances; disturbance of sphincter control and sexual function; mental disorders usually diagnosed in infancy, childhood or adolescence, including: mental retardation, learning disorders, motor skill disorders, communication disorders, pervasive developmental disorders, attention deficit and disruptive behaviour disorders, feeding and eating disorders, TIC disorders, elimination disorders; delirium and other cognitive disorders; substance related disorders including: alcohol-related disorders, nicotine-related disorders, disorders related to cocaine, opioids, cannabis, hallucinogens and other drugs; schizophrenia and other psychotic disorders; mood disorders, including depressive disorders and bipolar disorders; anxiety disorders, including panic disorders, phobias, obsessive-compulsive disorders, stress disorders (e.g., post-traumatic stress disorder), generalized anxiety disorders; eating disorders, including anorexia and bulimia; sleep disorders, including dyssomnias (insomnia, hypersomnia, narcolepsy, breathing related sleep disorder) and parasomnias; medication-induced movement disorders (including neuroleptic-induced parkinsonism and tardive dyskinesia); endocrine and metabolic diseases including diabetes, disorders of the endocrine glands, hypoglycaemia; acute and chronic pain; nausea and vomiting; irritable bowel syndrome; or cancers.

In particular, the conditions associated with altered glutamatergic signalling and/or functions, or conditions which can be affected by alteration of glutamate level or signalling, which are to be treated and/or prevented by the compound or the pharmaceutical composition according to the invention, include: dementias and related diseases, including dementias of the Alzheimer's type (DAT), Alzheimer's disease, Pick's disease, vascular dementias, Lewy-body disease, dementias due to metabolic, toxic and deficiency diseases (including alcoholism, hypothyroidism, and vitamin B12 deficiency), AIDS-dementia complex, Creutzfeld-Jacob disease and atypical subacute spongiform encephalopathy; parkinsonism and movement disorders, including Parkinson's disease, multiple system atrophy, progressive supranuclear palsy, corticobasal degeneration, hepatolenticular degeneration, chorea (including Huntington's disease and hemiballismus), athetosis, dystonias (including spasmodic torticollis, occupational movement disorder, Gilles de la Tourette syndrome), tardive or drug induced dyskinesias (including levodopa-induced dyskinesia), tremor and myoclonus; acute and chronic pain; anxiety disorders, including panic disorders, phobias, obsessive-compulsive disorders, stress disorders (including post-traumatic stress disorder) and generalized anxiety disorders; schizophrenia and other psychotic disorders; mood disorders, including depressive disorders and bipolar disorders; endocrine and metabolic diseases including diabetes, disorders of the endocrine glands and hypoglycaemia; or cancers.

The present invention thus relates to the compound of formula (I) or a pharmaceutically acceptable salt, solvate or prodrug thereof, or a pharmaceutical composition comprising any of the aforementioned entities in combination with a pharmaceutically acceptable excipient, for use in the treatment or prevention of a disease/disorder/condition selected from: dementias and related diseases, including dementias of the Alzheimer's type (DAT), Alzheimer's disease, Pick's disease, vascular dementias, Lewy-body disease, dementias due to metabolic, toxic and deficiency diseases (including alcoholism, hypothyroidism, and vitamin B12 deficiency), AIDS-dementia complex, Creutzfeld-Jacob disease and atypical subacute spongiform encephalopathy; parkinsonism and movement disorders, including Parkinson's disease, multiple system atrophy, progressive supranuclear palsy, corticobasal degeneration, hepatolenticular degeneration, chorea (including Huntington's disease and hemiballismus), athetosis, dystonias (including spasmodic torticollis, occupational movement disorder, Gilles de la Tourette syndrome), tardive or drug induced dyskinesias (including levodopa-induced dyskinesia), tremor and myoclonus; acute and chronic pain; anxiety disorders, including panic disorders, phobias, obsessive-compulsive disorders, stress disorders (including post-traumatic stress disorder) and generalized anxiety disorders; schizophrenia and other psychotic disorders; mood disorders, including depressive disorders and bipolar disorders; endocrine and metabolic diseases including diabetes, disorders of the endocrine glands and hypoglycaemia; or cancers. The invention particularly relates to the compound of formula (I) or a pharmaceutically acceptable salt, solvate or prodrug thereof, or a pharmaceutical composition comprising any of the aforementioned entities in combination with a pharmaceutically acceptable excipient, for use in the treatment or prevention of Parkinson's disease.

The scope of the invention embraces all pharmaceutically acceptable salt forms of the compound of formula (I) which may be formed, e.g., by protonation of an atom carrying an electron lone pair which is susceptible to protonation, such as an amino group, with an inorganic or organic acid, or as a salt of a hydroxy group with a physiologically acceptable cation as they are well known in the art. Exemplary base addition salts comprise, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Exemplary acid addition salts comprise, for example, mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts such as aspartate or glutamate salts. Preferred pharmaceutically acceptable salts of the compound of formula (I) include a hydrochloride salt, a hydrobromide salt, a mesylate salt, a sulfate salt, a tartrate salt, a fumarate salt, an acetate salt, a citrate salt, and a phosphate salt. A particularly preferred pharmaceutically acceptable salt of the compound of formula (I) is a hydrochloride salt. Accordingly, it is preferred that the compound of formula (I) is in the form of a hydrochloride salt, a hydrobromide salt, a mesylate salt, a sulfate salt, a tartrate salt, a fumarate salt, an acetate salt, a citrate salt, or a phosphate salt. More preferably, the compound of formula (I) is in the form of a hydrochloride salt.

Even more preferably, the compound of formula (I) is in the form of a bishydrochloride monohydrate salt (i.e., .2 HCl.H$_2$O).

Moreover, the scope of the invention embraces solid forms of the compound of the formula (I) in any solvated form, including e.g. solvates with water, for example hydrates, or with organic solvents such as, e.g., methanol, ethanol or acetonitrile, i.e. as a methanolate, ethanolate or acetonitrilate, respectively; or in the form of any polymorph. It is to be understood that such solvates of the compound of the formula (I) also include solvates of a pharmaceutically acceptable salt of the compound of the formula (I).

Furthermore, the present invention embraces all possible isomers, including configurational or conformational isomers, of the compound of formula (I), either in admixture or in pure or substantially pure form. In particular, the compound of formula (I) may have the (E)-configuration or the (Z)-configuration at the oxime group (=N—OH) as shown below, and the present invention embraces the (E)-isomer of the compound of formula (I), the (Z)-isomer of the compound of formula (I), and mixtures of the (E)-isomer and the (Z)-isomer of the compound of formula (I).

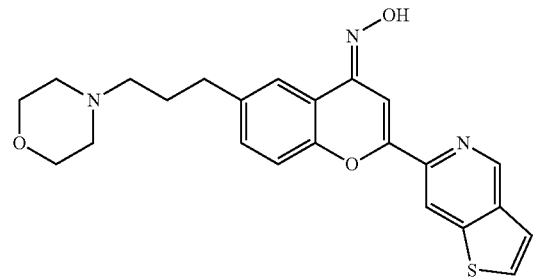

(E)-isomer of the compound of formula (I)

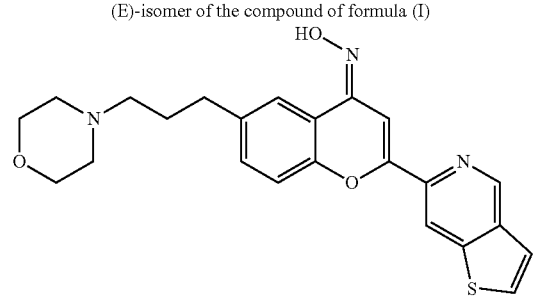

(Z)-isomer of the compound of formula (I)

It is preferred that the compound of formula (I) is the (E)-isomer, which is particularly advantageous in terms of its activity. Accordingly, it is preferred that at least 70 mol-%, more preferably at least 80 mol-%, even more preferably at least 90 mol-%, even more preferably at least 95 mol-%, even more preferably at least 98 mol-%, and yet even more preferably at least 99 mol-% of the compound of formula (I) is present in the form of the (E)-isomer. Likewise, it is preferred that at least 70 mol-%, more preferably at least 80 mol-%, even more preferably at least 90 mol-%, even more preferably at least 95 mol-%, even more preferably at least 98 mol-%, and yet even more preferably at least 99 mol-% of the compound of formula (I) or the pharmaceutically acceptable salt, solvate or prodrug thereof which is contained in the pharmaceutical composition of the present invention is in the form of the (E)-isomer, i.e., has the (E)-configuration at the oxime group comprised in the compound of formula (I).

Pharmaceutically acceptable prodrugs of the compound of the formula (I) are derivatives which have chemically or metabolically cleavable groups and become, by solvolysis or under physiological conditions, the compound of the formula (I) which is pharmaceutically active in vivo. Prodrugs of the compound of the formula (I) may be formed in a conventional manner with a functional group of the compound, such as a hydroxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). Such prodrugs include, e.g., an acyloxy derivative prepared by reacting the hydroxyl group of the compound of formula (I) with a suitable acylhalide or a suitable acid anhydride. An especially preferred acyloxy derivative as a prodrug is —OC(=O)—CH$_3$, —OC(=O)—C$_2$H$_5$, —OC(=O)—C$_3$H$_7$, —OC(=O)-(tert-butyl), —OC(=O)—C$_{15}$H$_{31}$, —OC(=O)—CH$_2$CH$_2$COONa, —O(C=O)—CH(NH$_2$)CH$_3$ or —OC(=O)—CH$_2$—N(CH$_3$)$_2$. Accordingly, the pharmaceutically acceptable prodrug may be a compound of formula (I), wherein the oxime —OH group is in the form of an O-acyl-oxime (or acyloxy derivative) such as, e.g., —OC(=O)—CH$_3$, —OC(=O)—C$_2$H$_5$, —OC(=O)—C$_3$H$_7$, —OC(=O)-(tert-butyl), —OC(=O)—C$_{15}$H$_{31}$, —OC(=O)—CH$_2$CH$_2$COONa, —O(C=O)—CH(NH$_2$)CH$_3$ or —OC(=O)—CH$_2$—N(CH$_3$)$_2$. The oxime —OH group of the compound of formula (I) may also be in the form of an O-alkyl-oxime such as, e.g., —O—CH$_3$, —O—C$_2$H$_5$, —O—C$_3$H$_7$ or —O-(tert-butyl). The oxime —OH group of the compound of formula (I) may also be in the form of an O-dialkylphosphinyloxy such as —O—P(=O)—[O—(CH$_3$)$_2$], —O—P(=O)—[O—(C$_2$-C$_5$)$_2$], —O—P(=O)—[O—(C$_3$-C$_7$)$_2$] or —O—P(=O)—[O-(tert-butyl)$_2$] or in the form of an O-phosphoric acid —O—P(=O)—(OH)$_2$ or in the form of an O-sulfuric acid —O—SO$_2$—OH. Thus, the pharmaceutically acceptable prodrug according to the present invention is preferably a compound of formula (I), wherein the oxime —OH group is in the form of an O-acyl-oxime group, an O-alkyl-oxime group, an O-dialkylphosphinyloxy group, an O-phosphoric acid group, or an O-sulfuric acid group.

The compound of formula (I) may be administered per se or may be formulated as a medicament. Within the scope of the present invention are pharmaceutical compositions comprising as an active ingredient the compound of the formula (I) as defined herein above. The pharmaceutical compositions may optionally comprise one or more pharmaceutically acceptable excipients, such as carriers, diluents, fillers, disintegrants, lubricating agents, binders, colorants, pigments, stabilizers, preservatives, or antioxidants.

The pharmaceutical compositions can be formulated by techniques known to the person skilled in the art, such as the techniques published in Remington's Pharmaceutical Sciences, 20$^{th}$ Edition. The pharmaceutical compositions can be formulated as dosage forms for oral, parenteral, such as intramuscular, intravenous, subcutaneous, intradermal, intraarterial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compound of formula (I) according to the invention or the above described pharmaceutical compositions comprising the compound of formula (I) may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual), parenteral (e. g., using injection techniques or infusion techniques, and including, for example, by injection, e.g. subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g. through mouth or nose), gastrointestinal, intrauterine, intraocular, subcutaneous, ophthalmic (including intravitreal or intracameral), rectal, and vaginal. It is particularly preferred that the compound of formula (I) according to the present invention or the pharmaceutical compositions of the invention are to be administered orally.

If said compound or pharmaceutical compositions are administered parenterally, then examples of such administration include one or more of: intravenously, intraarterially, intraperitoneally, intrathecally, intraventricularly, intraurethrally, intrasternally, intracranially, intramuscularly or subcutaneously administering the compound or the pharmaceutical compositions, and/or by using infusion techniques. For parenteral administration, the compound is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compound or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications. The peroral administration of the compound or pharmaceutical composition according to the invention is particularly preferred.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Alternatively, said compound or pharmaceutical compositions can be administered in the form of a suppository or pessary, or it may be applied topically in the form of a gel, hydrogel, lotion, solution, cream, ointment or dusting powder. The compound of the present invention may also be dermally or transdermally administered, for example, by the use of a skin patch.

Said compound or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For topical application to the skin, said compound or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compound of formula (I) for administration to a human (of approximately 70 kg body weight) may be 0.05 to 2000 mg, preferably 0.1 mg to 1000 mg, of the active ingredient per unit dose. The unit dose may be administered, for example, 1 to 4 times per day. The dose will depend on the route of administration. A further, particularly preferred dose of the compound of formula (I) for peroral administration to a mammal (such as a human) is about 1 to about 25 mg/kg bodyweight (e.g., 1 mg/kg, 2 mg/kg, 5 mg/kg, 10 mg/kg, 15 mg/kg, 20 mg/kg, or 25 mg/kg), which dose may be administered, e.g., 1, 2, 3 or 4 times per day (preferably twice per day). Even more preferably, the compound of formula (I) is to be administered to a subject (e.g., a mammal, preferably a human) twice a day at a dose, per each administration, of 2 to 25 mg/kg bodyweight. It will be appreciated that it may be necessary to make routine variations to the dosage depending on the age and weight of the patient/subject as well as the severity of the condition to be treated. The precise dose and route of administration will ultimately be at the discretion of the attendant physician or veterinarian.

The compound of formula (I) according to the invention can be administered in monotherapy (e.g., without concomitantly administering any further therapeutic agents, or without concomitantly administering any further therapeutic agents against the same disease that is to be treated or prevented with the compound of formula (I), such as Parkinson's disease). However, the compound of formula (I) can also be administered in combination with one or more other therapeutic agents. When the compound of formula (I) is used in combination with a second therapeutic agent active against the same disease or condition, the dose of each compound may differ from that when the corresponding compound is used alone. The combination of the compound of formula (I) with one or more other therapeutic agents may comprise the simultaneous/concomitant administration of the compound of formula (I) and the other therapeutic agent(s) (either in a single pharmaceutical formulation or in separate pharmaceutical formulations), or the sequential/separate administration of the compound of formula (I) and the other therapeutic agent(s). For example, if the compound of formula (I) is used for the treatment or prevention of parkinsonism or a movement disorder, particularly for the treatment or prevention of Parkinson's disease, an antiparkinson drug (such as, e.g., levodopa) may be administered in combination with the compound of formula (I).

Furthermore, the compound of formula (I) can also be radio-labeled by carrying out its synthesis (e.g., as described in Example 1) using precursors comprising at least one atom which is a radioisotope. Preferably, radioisotopes of carbon atoms, hydrogen atoms, sulfur atoms, or iodine atoms are employed, such as, e.g., $^{14}C$, $^{3}H$, $^{35}S$, or $^{125}I$. Compounds labeled with $^{3}H$ (tritium) can also be prepared by subjecting the compound of formula (I) to a hydrogen exchange reaction such as, e.g., a platinum-catalyzed exchange reaction in tritiated acetic acid (i.e., acetic acid comprising $^{3}H$ instead of $^{1}H$), an acid-catalyzed exchange reaction in tritiated trifluoroacetic acid, or a heterogeneous-catalyzed exchange reaction with tritium gas. For a person skilled in the field of synthetic chemistry, various further ways for radio-labeling the compound of formula (I) or preparing radio-labeled derivatives of this compound are readily apparent. Fluorescent labels can also be bound to the compound of formula (I) following methods known in the art.

The subject or patient, such as the subject in need of treatment or prevention/prophylaxis, may be an animal (e.g., a non-human animal), a vertebrate animal, a mammal, a rodent (e.g., a guinea pig, a hamster, a rat, a mouse), a murine (e.g., a mouse), a canine (e.g., a dog), a feline (e.g., a cat), an equine (e.g., a horse), a primate, a simian (e.g., a monkey or ape), a monkey (e.g., a marmoset, a baboon), an ape (e.g., a gorilla, chimpanzee, orang-utan, gibbon), or a human. In the context of this invention, it is particularly envisaged that animals are to be treated which are economically, agronomically or scientifically important. Scientifically important organisms include, but are not limited to, mice, rats, and rabbits. Lower organisms such as, e.g., fruit flies like *Drosophila melagonaster* and nematodes like *Caenorhabditis elegans* may also be used in scientific approaches. Non-limiting examples of agronomically important animals are sheep, cattle and pigs, while, for example, cats and dogs may be considered as economically important animals. Preferably, the subject/patient is a mammal; more preferably, the subject/patient is a human.

The term "treatment" of a disorder or disease as used herein is well known in the art. "Treatment" of a disorder or disease implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e., diagnose a disorder or disease).

The "treatment" of a disorder or disease may, for example, lead to a halt in the progression of the disorder or disease (e.g., no deterioration of symptoms) or a delay in the progression of the disorder or disease (in case the halt in progression is of a transient nature only). The "treatment" of a disorder or disease may also lead to a partial response (e.g., amelioration of symptoms) or complete response (e.g., disappearance of symptoms) of the subject/patient suffering from the disorder or disease. Accordingly, the "treatment" of a disorder or disease may also refer to an amelioration of the disorder or disease, which may, for example, lead to a halt in the progression of the disorder or disease or a delay in the progression of the disorder or disease. Such a partial or complete response may be followed by a relapse. It is to be understood that a subject/patient may experience a broad range of responses to a treatment (e.g., the exemplary responses as described herein above).

Treatment of a disorder or disease may, inter alia, comprise curative treatment (preferably leading to a complete response and eventually to healing of the disorder or disease) and palliative treatment (including symptomatic relief).

Also the term "prevention" or "prophylaxis" of a disorder or disease as used herein is well known in the art. For example, a patient/subject suspected of being prone to suffer from a disorder or disease as defined herein may, in particular, benefit from a prevention/prophylaxis of the disorder or disease. Said subject/patient may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in said patient/subject (for example, said patient/subject does not show any clinical or pathological symptoms). Thus, the term "prevention" or "prophylaxis" comprises the use of compound of the present invention before any clinical and/or pathological symptoms are diagnosed or determined or can be diagnosed or determined by the attending physician. The terms "prophylaxis" and "prevention" are used herein interchangeably.

In this specification, a number of documents including patent applications and scientific literature are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention is also described by the following illustrative figures. The appended figures show:

FIG. 1: PXT002331 and PXT001858 brain exposure after oral administration in rats (10 mg/kg).

Figure 2:
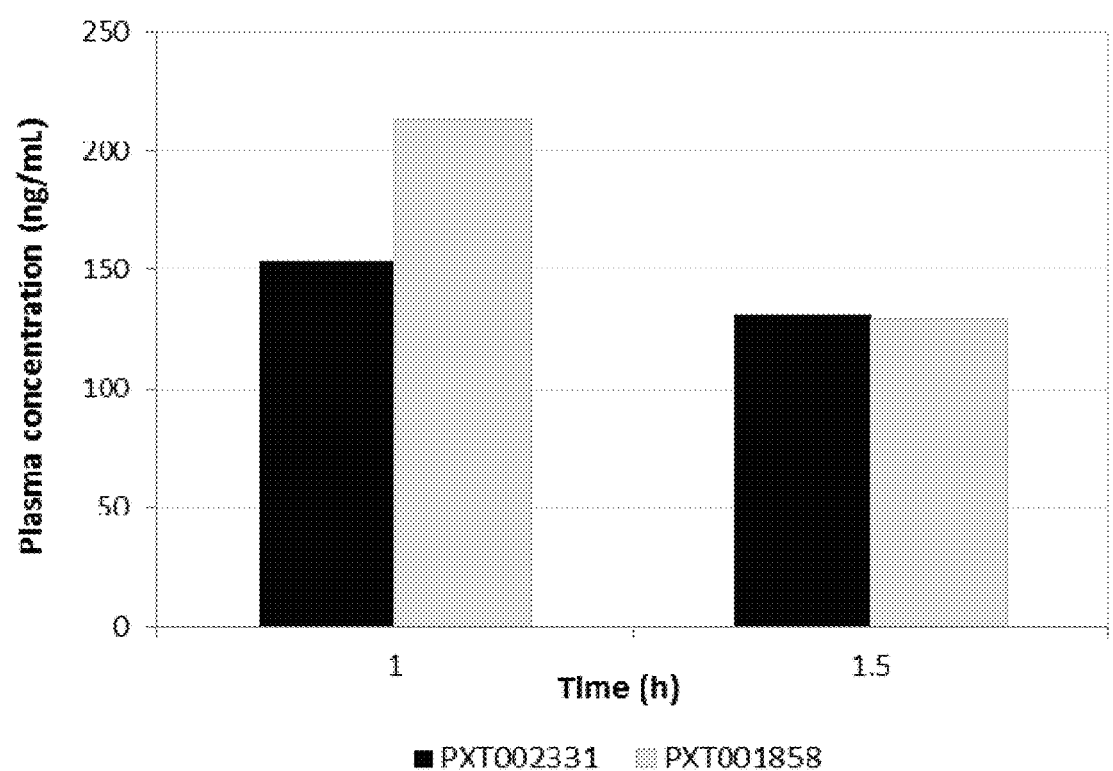

FIG. 2: PXT002331 and PXT001858 plasma concentration after oral administration in rats (10 mg/kg).

Figure 3:
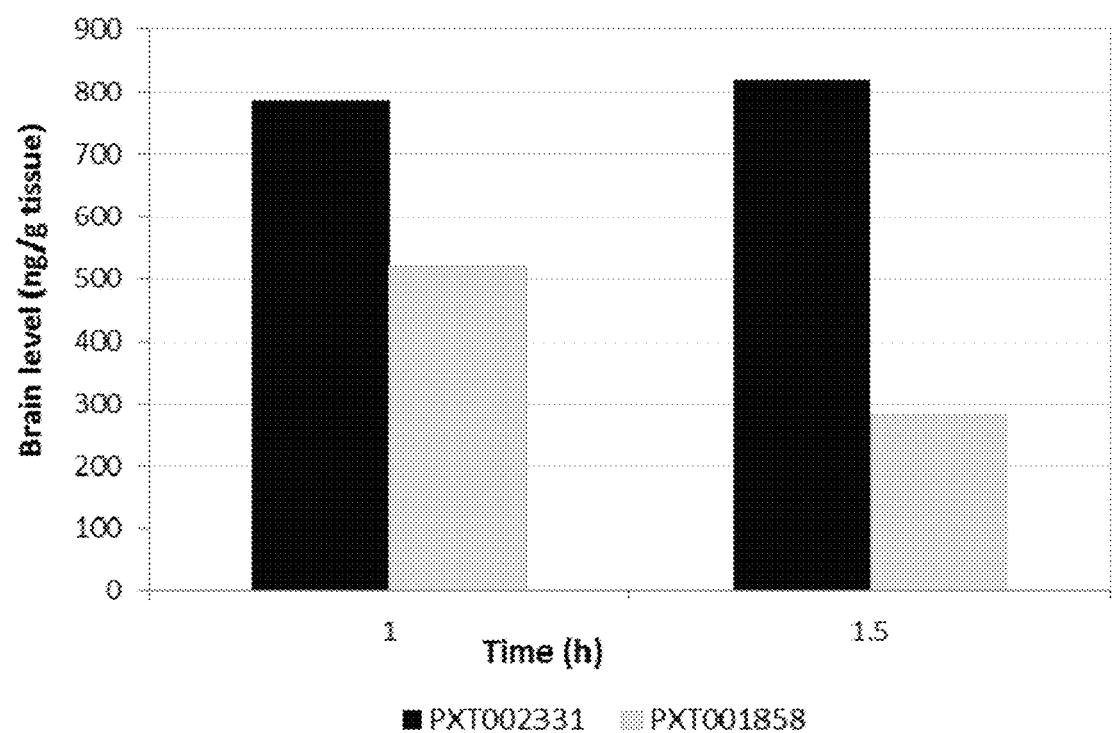

FIG. 3: PXT002331 and PXT001858 brain level after oral administration in rats (10 mg/kg).

Figure 4:
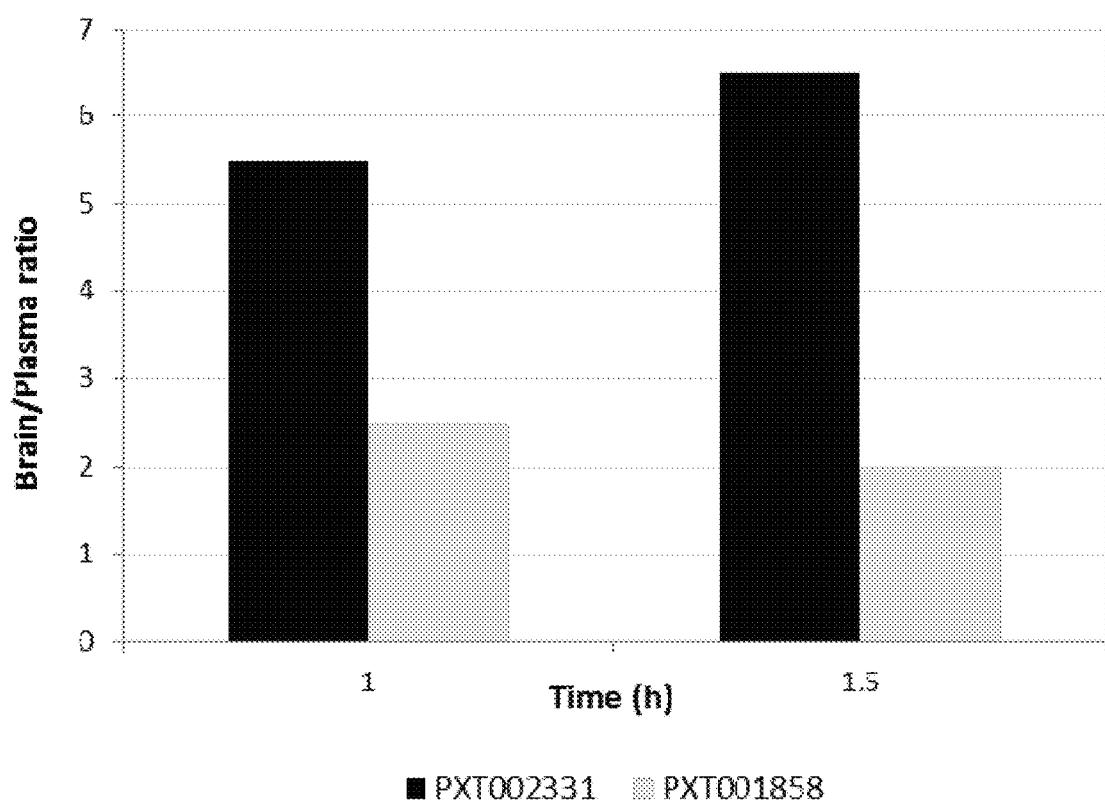

FIG. 4: PXT002331 and PXT001858 brain/plasma ratio after oral administration in rats (10 mg/kg).

FIGS. 5A-F: Evaluation of the anti-parkinsonian efficacy of PXT002331 in the 1-methyl-4-phenyl-1,2,3,6-tetrahydropyridine (MPTP) macaque model of Parkinson's disease (see Example 3). (A) PXT002331 as a stand-alone treatment; oral administration twice a day during 4 days, assessment of parkinsonian scores at day 4; data are mean+s.e.m. over 2 hours observation (n=7 per group; 1 of the 8 monkeys initially used was excluded); "Veh"=vehicle; "LD opt"=L-dopa optimal dose"; *=P<0.05 vs Veh; ***=P<0.001 vs Veh; statistical analysis: Friedman followed by Dunn's. (B) Combined treatment using PXT002331 (25 mg/kg)+low dose of L-dopa (4-9 mg/kg)–parkinsonism time course; oral administration twice a day during 4 days, assessment at day #4; L-dopa optimal dose ("LDopt"): >20 mg/kg; L-dopa suboptimal dose ("LDso"): 4-9 mg/kg; combined administration of L-dopa (suboptimal dose) and PXT002331: twice a day/4 days. (C) Combined treatment using PXT002331+low dose of L-dopa-difference in parkinsonian score for monkeys treated with low dose of L-dopa and PXT002331 in comparison to low dose of L-dopa alone, and in comparison to optimal dose of L-dopa; assessment at day 4, between 1 and 2 h after L-dopa administration (i.e., 2 and 3 h after PXT002331 administration); all monkeys treated with PXT002331+L-dopa showed a significant improvement in parkinsonian score. (D) Combined treatment using PXT002331+low dose of L-dopa–dose-response evaluation for different doses of PXT002331; assessment of parkinsonian scores at day 4; "Veh"=vehicle; "low LD"=low dose of L-dopa; "LD opt"=optimal dose of L-dopa; *=P<0.05 vs low LD; statistical analysis: non-parametric one-way repeated, measures ANOVA (Friedman's test), followed by Dunn's multiple comparison; N=7. (E) Computerized locomotor activity in early-stage PD monkey model for PXT002331 in combination with L-dopa (low dose or optimal dose) upon oral administration; *=P<0.05 vs vehicle; =P<0.01 vs vehicle; *=P<0.001 vs vehicle; statistical analysis: Friedman followed by Dunnett's; N=5 (6 monkeys/1 excluded). (F) Combined treatment using PXT002331+optimal dose of L-dopa–disability score and dyskinesia score.

The present invention particularly relates to the following items:

1. A compound of the following formula (I):

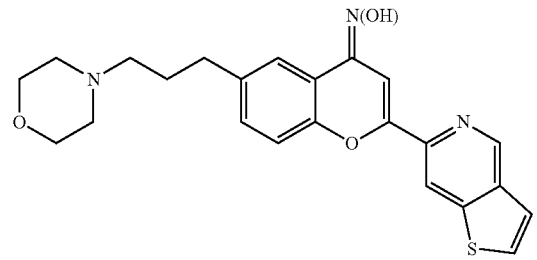

or a pharmaceutically acceptable salt, solvate or prodrug thereof.

2. The compound of item 1, wherein said compound has the (E)-configuration at the oxime group comprised in formula (I).

3. The compound of item 1 or 2, wherein the pharmaceutically acceptable salt is a hydrochloride salt.

4. The compound of any one of items 1 to 3 for use as a medicament.

5. A pharmaceutical composition comprising the compound of any one of items 1 to 3 and a pharmaceutically acceptable excipient.

6. The compound of any one of items 1 to 3 or the pharmaceutical composition of item 5 for use in the treatment or prevention of a condition associated with altered glutamatergic signalling and/or functions, or a condition which can be affected by alteration of glutamate level or signalling.

7. Use of the compound of any one of items 1 to 3 for the preparation of a medicament for the treatment or prevention of a condition associated with altered glutamatergic signalling and/or functions, or a condition which can be affected by alteration of glutamate level or signalling.
8. A method of treating or preventing a condition associated with altered glutamatergic signalling and/or functions, or a condition which can be affected by alteration of glutamate level or signalling, the method comprising the administration of the compound of any one of items 1 to 3 or the pharmaceutical composition of item 5 to a subject in need thereof.
9. The compound or the pharmaceutical composition for use according to item 6 or the use of item 7 or the method of item 8, wherein said condition associated with altered glutamatergic signalling and/or functions, or said condition which can be affected by alteration of glutamate level or signalling is selected from: dementias, parkinsonism and movement disorders, acute or chronic pain, anxiety disorders, schizophrenia, mood disorders, endocrine and metabolic diseases, diabetes, disorders of the endocrine glands, hypoglycaemia, or cancers.
10. The compound or the pharmaceutical composition for use according to item 9 or the use of item 9 or the method of item 9, wherein said dementias are selected from: dementias of the Alzheimer's type (DAT); Alzheimer's disease; Pick's disease; vascular dementias; Lewy-body disease; dementias due to metabolic, toxic and deficiency diseases, including alcoholism, hypothyroidism, and vitamin B12 deficiency; AIDS-dementia complex; Creutzfeld-Jacob disease; or atypical subacute spongiform encephalopathy.
11. The compound or the pharmaceutical composition for use according to item 9 or the use of item 9 or the method of item 9, wherein said parkinsonism and movement disorders are selected from: Parkinson's disease; multiple system atrophy; progressive supranuclear palsy; corticobasal degeneration; hepatolenticular degeneration; chorea, including Huntington's disease and hemiballismus; athetosis; dystonias, including spasmodic torticollis, occupational movement disorder, and Gilles de la Tourette syndrome; tardive or drug induced dyskinesias, including levodopa-induced dyskinesia; tremor; or myoclonus.
12. The compound or the pharmaceutical composition for use according to item 9 or the use of item 9 or the method of item 9, wherein said anxiety disorders are selected from: panic disorders; phobias; obsessive-compulsive disorders; stress disorders, including post-traumatic stress disorder; or generalized anxiety disorders.
13. The compound or the pharmaceutical composition for use according to item 9 or the use of item 9 or the method of item 9, wherein said mood disorders are selected from depressive disorders or bipolar disorders.
14. The compound of any one of items 1 to 3 or the pharmaceutical composition of item 5 for use in the treatment or prevention of Parkinson's disease.
15. Use of the compound of any one of items 1 to 3 for the preparation of a medicament for the treatment or prevention of Parkinson's disease.
16. A method of treating or preventing Parkinson's disease, the method comprising the administration of the compound of any one of items 1 to 3 or the pharmaceutical composition of item 5 to a subject in need thereof.
17. The compound or the pharmaceutical composition for use according to any one of items 6 or 9 to 14 or the use of any one of items 7, 9 to 13 or 15 or the method of any one of items 8 to 13 or 16, wherein said compound, said pharmaceutical composition or said medicament is to be administered orally.
18. The method of any one of items 8 to 14, 16 or 17, wherein said subject is a human.

The invention will now be described by reference to the following examples which are merely illustrative and are not to be construed as a limitation of the scope of the present invention.

EXAMPLES

Example 1: Preparation of the Compound of Formula (I)

1) General Synthetic Route

The compound of formula (I) according to the invention (i.e., PXT002331) can be prepared from readily available starting materials by several synthetic approaches, using solution-phase or solid-phase chemistry protocols, or mixed solution and solid phase protocols. For example, the compound of formula (I) can be prepared using the synthetic schemes depicted below.

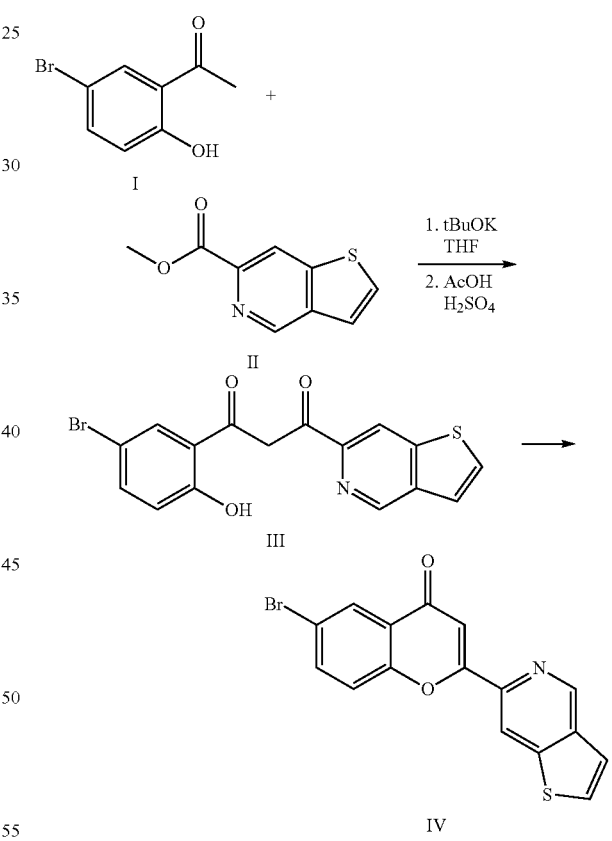

The commercially available bromo acetophenone I is reacted with commercial thieno[3,2-c]pyridine methyl ester II in a solvent such as tetrahydrofuran (THF) and in the presence of a weak base like potassium tert-butoxide (tBuOK) to yield the intermediate diketone III. This procedure is known as Baker Venkataraman rearrangement (Baker, W., *J. Chem. Soc*, 1933, 1381).

The intermediate diketone III is then cyclized under acidic conditions in the presence of a strong dehydrating agent like sulfuric acid ($H_2SO_4$) in refluxing acetic acid (AcOH) to yield the chromone IV.

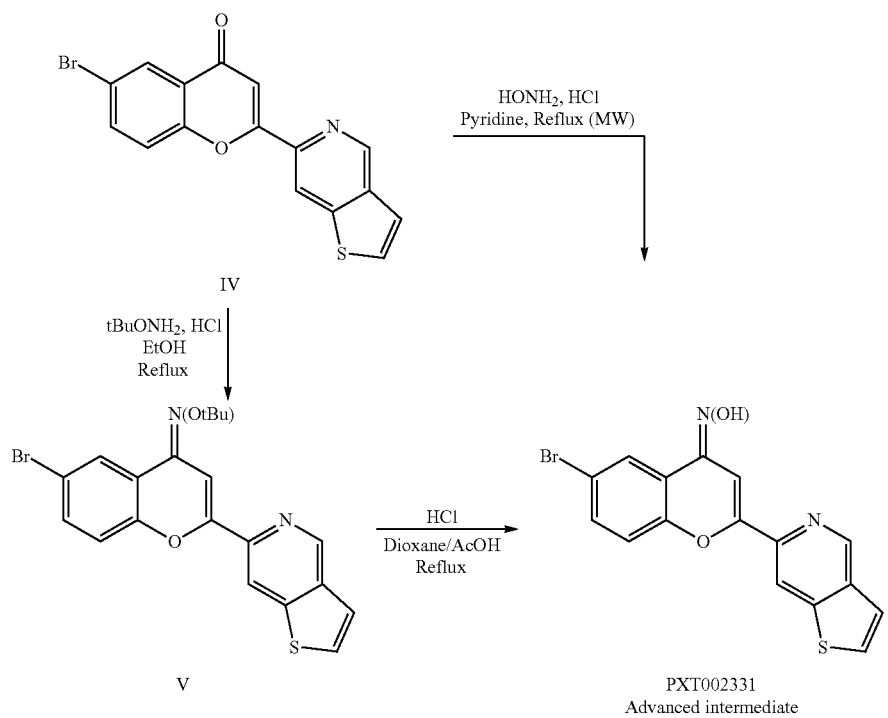

Introduction of the oxime may be obtained by reacting the derivative IV with hydroxyl amine hydrochloride (HONH₂, HCl) in pyridine or ethanol under microwave conditions to yield directly the chromone oxime advanced intermediate that would lead to PXT002331 in a couple of reaction steps. This advanced intermediate leading to PXT002331 can be also obtained by using a two-step procedure as depicted above using tert-butyl hydroxylamine hydrochloride (tBuONH₂, HCl) in ethanol followed in a subsequent step by deprotection of the tert-butyl group under acidic conditions like hydrochloric acid (HCl) in a mixture of polar solvent such as THF and acetic acid.

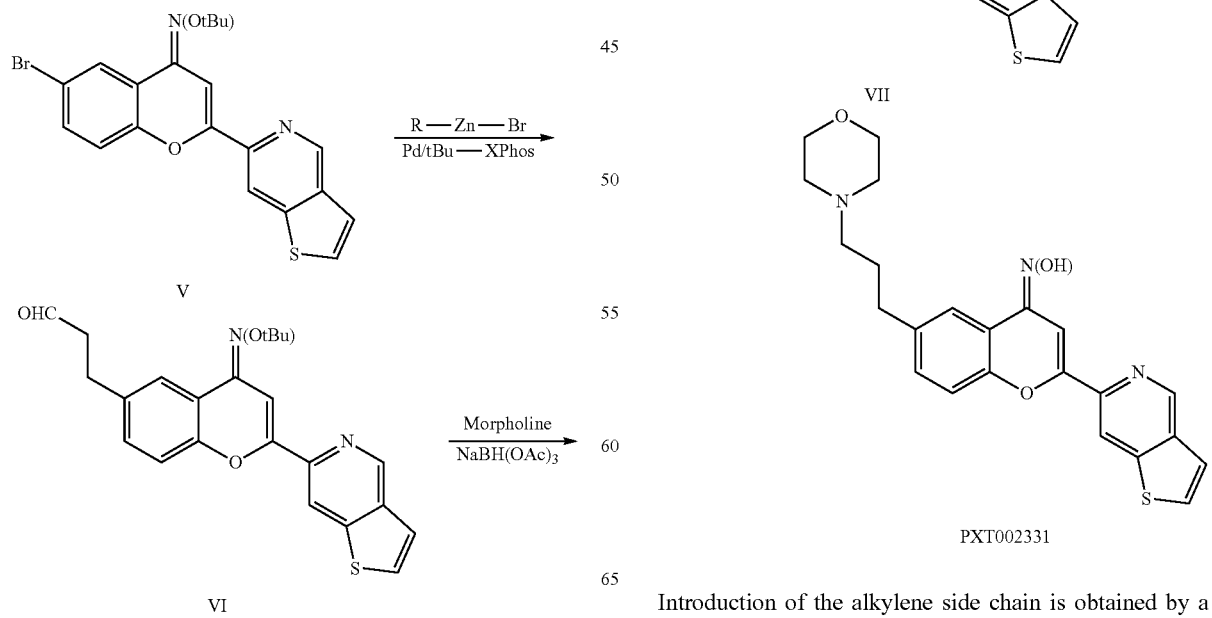

Introduction of the alkylene side chain is obtained by a palladium catalyzed cross-coupling reaction such as Negishi cross-coupling using a commercially available zinc reagent and appropriate ligand/palladium catalytic system. Subsequent functionalization followed by standard reductive amination using weak reducing agents such as triacetoxy borohydride yield advanced intermediate VII in good yields. Final deprotection of the oxime protecting group under acidic conditions lead to the compound of formula (I), i.e. PXT002331.

2) Synthesis of the Compound of Formula (I)

The commercially available starting materials used in the following experimental description were purchased from Aldrich, Sigma, ACROS or ABCR unless otherwise reported.

The compounds described in the following have been named according to the standards used in the program AutoNom v1.0.1.1 (MDL Information Systems, Inc.).

$^1$H NMR analyses were carried out using BRUKER NMR, model DPX-400 MHz FT-NMR. Residual signal of deuterated solvent was used as internal reference. Chemical shifts (δ) are reported in ppm in relative to the residual solvent signal (δ=2.50 for $^1$H NMR in DMSO-$d_6$, and 7.26 in CDCl$_3$). s (singlet), d (doublet), t (triplet), q (quadruplet), br (broad). Some compounds in the experimental part exist as mixture of E/Z isomers in different ratios. E/Z isomer ratio was well determined for the final compound PXT002331.

The MS data provided herein below were obtained as followed: Mass spectrum: LC/MS Waters ZMD (ESI).

HPLC analyses were obtained as followed using a Waters X-Bridge™ C8 50 mm×4.6 mm column at a flow of 2 mL/min; 8 min gradient H$_2$O:CH$_3$CN:TFA from 100:0:0.1% to 0:100:0.05% with UV detection (254 nm).

The mass directed preparative HPLC purifications were performed with a mass directed auto purification Fraction lynx from Waters equipped with a Sunfire Prep C18 OBD column 19×100 mm 5 µm, unless otherwise reported. All purifications were performed with a gradient of ACN/H$_2$O or ACN/H$_2$O/HCOOH (0.1%).

The compound of formula (I) was prepared as shown in the following reaction scheme:

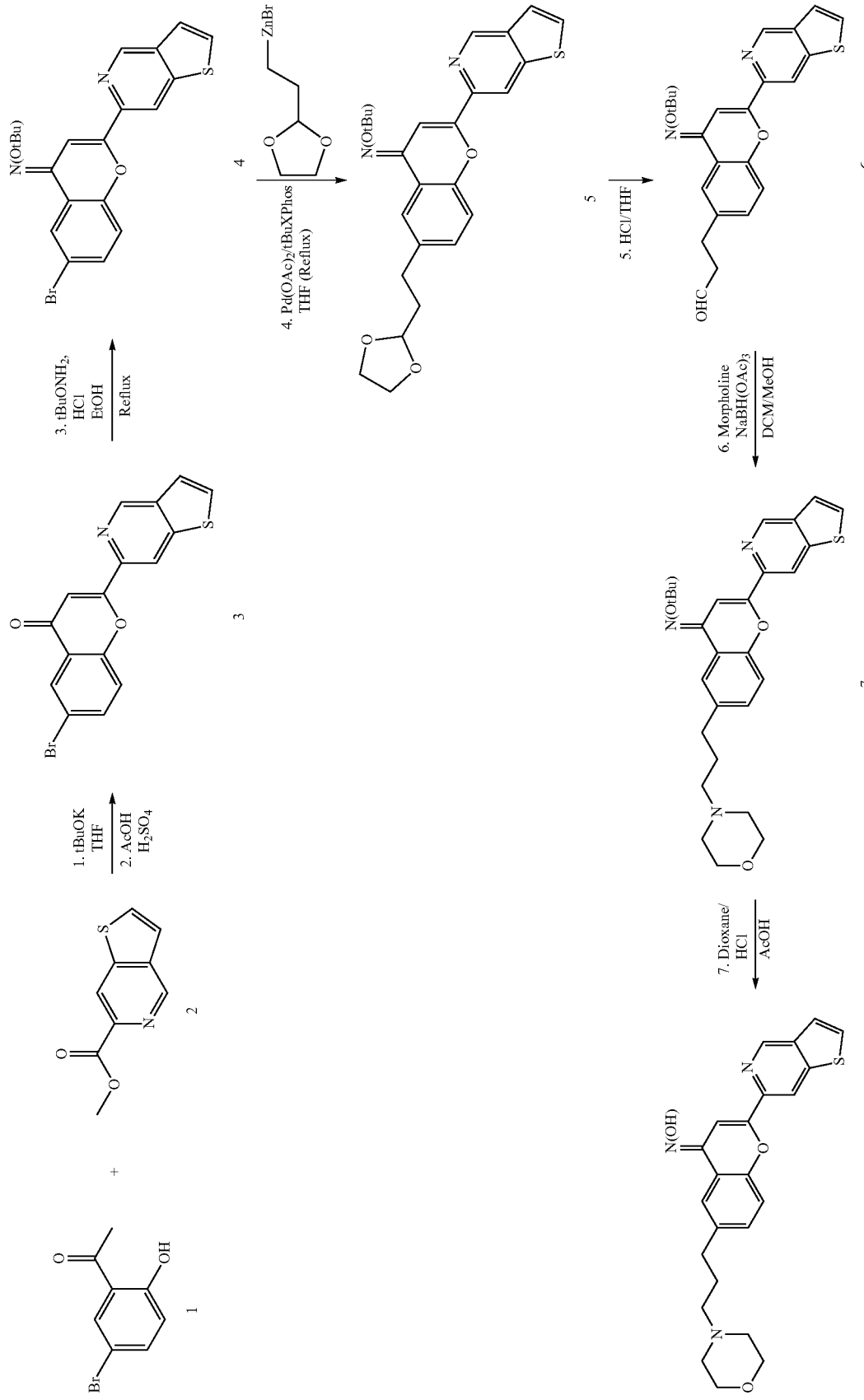
Reaction Scheme

Steps 1 and 2: 6-Bromo-2-(thieno[3,2-c]pyridin-6-yl)-4H-chromen-4-one (3)

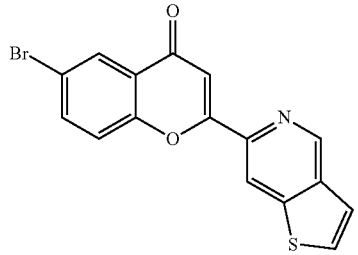 [SMILES: O=c1cc(-c2cc3sccc3cn2)oc2ccc(Br)cc12]

To a suspension of potassium tert-butoxide (156.0 g, 1.39 mol, 3.0 eq) in THF (500 mL) at 0° C. was added a solution of 5-bromo-2-hydroxyacetophenone (100.0 g, 0.47 mol, 1 eq) in THF (500 mL). The reaction mixture was stirred vigorously for 10 minutes. A solution of thienopyridine ester (98 g, 0.51 mol, 1.1 eq) in THF (1.0 L) was added to the reaction mixture. The resulting reddish suspension was refluxed for 1 h, at which time LC/MS analysis indicated completion of the reaction. The reaction mixture was cooled to room temperature (RT) to give a thick orange suspension and poured into ice water (5.0 L). The aqueous layer was neutralized by addition of an aqueous HCl solution (1.5 N) under vigorous stirring. The resulting yellow solid was collected by filtration, washed with water and dried under suction. The crude mass was again further dried overnight under pressure at 45° C. for 16 h, which yielded 156 g of a yellow solid.

The yellow solid (156 g) was then suspended at RT in glacial acetic acid (1.0 L) and concentrated $H_2SO_4$ (10 mL). This mixture was heated at 110° C. for 2 hours. The reaction mixture turned into a brown suspension. After confirming completion of the reaction (by LC/MS), the crude mass was suspended in ice water (2.0 L) and neutralized by addition of an aqueous NaOH solution (1 N). The precipitated beige solid obtained was collected by filtration, washed with water and dried under suction. The material was further dried one night at 50° C. under high vacuum to yield 140.0 g of the title compound as a beige solid.

Yield: 83%.
LC/MS: Mass found (m/z, M+1, 358.0), Area 94.78%.
$^1$H NMR (DMSO-$d_6$, 400 MHz) δ 9.32 (s, 1H), 9.06 (s, 1H), 8.15 (m, 2H), 8.06 (m, 1H), 7.84 (d, J 5.4 Hz, 1H), 7.77 (d, J 5.4 Hz, 1H), 7.32 (s, 1H).

Step 3: 6-Bromo-2-(thieno[3,2-c]pyridin-6-yl)-4H-chromen-4-one O-tert-butyl-oxime (4)

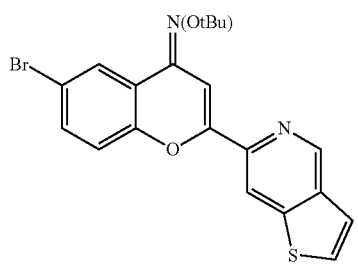

In a sealed tube, a suspension of 6-bromo-2-(thieno[3,2-c]pyridin-6-yl)-4H-chromen-4-one (20.0 g, 56 mmol, 1 eq) and O-tert-butyl hydroxylamine hydrochloride (14.0 g, 112 mmol, 2 eq) in anhydrous EtOH (300 mL) was heated at 115° C. for 20 hours. After confirming the reaction completion by TLC, the reaction mixture was filtered and the yellow solid washed twice with cold EtOH (50 mL) and dried under vacuum to yield 20 g of the title compound as a yellow solid.

Yield: 83%.
LC/MS: Mass found (m/z, M+1, 429.0), Area 97.83%.
$^1$H NMR (DMSO-$d_6$, 400 MHz) δ 9.25 (s, 1H), 8.78 (s, 1H), 8.05 (m, 2H), 7.71 (m, 2H), 7.59 (s, 1H), 7.48 (s, 1H), 1.40 (s, 9H).

Step 4: 6-(2-[1,3]Dioxolan-2-yl-ethyl)-2-(thieno[3,2-c]pyridin-6-yl)-4H-chromen-4-one O-tert-butyl-oxime (5)

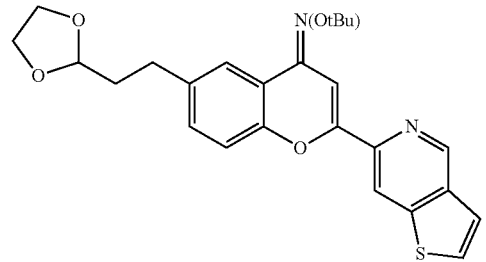

To a degassed solution of 6-bromo-2-(thieno[3,2-c]pyridin-6-yl)-4H-chromen-4-one O-tert-butyl-oxime (100.0 g, 233 mmol, 1 eq) and 2-di-tert-butylphosphino-2',4',6'-triisopropylbiphenyl (4.9 g, 11.6 mmol, 0.05 eq) in anhydrous THF (500 mL) was added palladium (II) acetate (2.6 g, 11.6 mmol, 0.05 eq) followed by 2-(1,3-dioxolan-2-yl)ethylzinc bromide solution (0.5 M in THF, 652 mL, 362 mmol, 1.5 eq). The reaction mixture was heated at 100° C. for 14 hours. After confirming completion of the reaction by LC/MS, the reaction mixture was quenched with water (20 mL) and concentrated under vacuum. The resulting crude yellow oil was purified by chromatography on silica gel using cyclohexane/ethyl acetate (80/20) as eluent to afford 85 g of the title compound as a yellow solid.

Yield: 82%
HPLC: 93.00% (254 nm), RT: 2.50 min.
LC/MS: Mass found (m/z, M+1, 451.0), Area 93.96%.
$^1$H NMR (DMSO-$d_6$, 400 MHz) δ 9.27 (s, 1H), 8.77 (s, 1H), 8.05 (d, J 5.4 Hz, 1H), 7.78 (s, 1H), 7.73 (d, J 5.4 Hz, 1H), 7.62 (s, 1H), 7.43 (m, 2H), 4.85 (m, 1H), 3.93 (m, 2H), 3.80 (m, 2H), 2.75 (m, 2H), 1.90 (s, 2H), 1.39 (s, 9H).

Step 5: 3-(4-tert-Butoxyimino-2-(thieno[3,2-c]pyridin-6-yl)-4H-chromen-6-yl)-propionaldehyde (6)

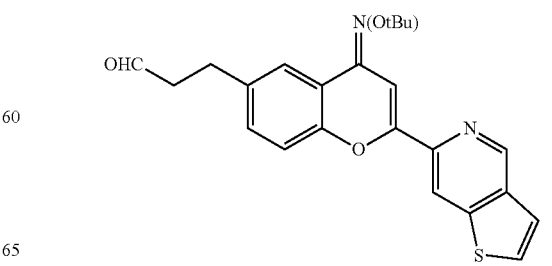

To a solution of 6-(2-[1,3]dioxolan-2-yl-ethyl)-2-(thieno[3,2-c]pyridin-6-yl)-4H-chromen-4-one O-tert-butyl-oxime (100.0 g, 222 mmol, 1 eq) in THF (1.0 L) was slowly added an aqueous solution of HCl (3 N, 1.0 L). The resulting yellow mixture was stirred at room temperature for 24 hours to give a thick yellow emulsion. After completion of the reaction (LC/MS), the reaction mixture was neutralized by addition of an aqueous saturated solution of $NaHCO_3$ and extracted with $CH_2Cl_2$ (2×5.0 L). The combined organic extracts were washed with brine (2.0 L), dried over magnesium sulfate, filtered and concentrated under vacuum to yield 89 g of the title compound as a yellow solid. The resulting yellow solid was taken crude to the next step without further purification.

Yield: 92%

LC/MS: Mass found (m/z, M+1, 407.3), Area 91%.

$^1$H NMR ($CDCl_3$, 400 MHz) δ 9.79 (s, 1H), 9.09 (s, 1H), 8.39 (s, 1H), 7.82 (s, 1H), 7.67 (s, 1H), 7.52 (d, J 5.4 Hz, 1H), 7.43 (d, J 5.4 Hz, 1H), 7.17 (m, 2H), 2.93 (m, 2H), 2.77 (s, 2H), 1.37 (s, 9H).

Step 6: 6-(3-Morpholin-4-yl-propyl)-2-(thieno[3,2-c]pyridin-6-yl)-4H-chromen-4-one O-tert-butyl oxime (7)

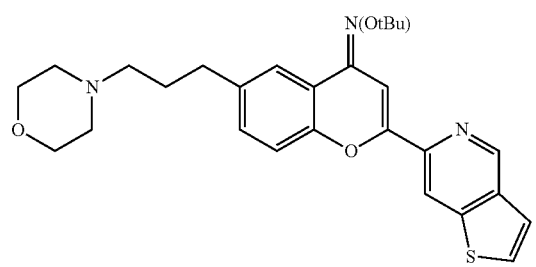

To a mixture of 3-(4-tert-butoxyimino-(2-thieno[3,2-c]pyridin-6-yl)-4H-chromen-6-yl)-propionaldehyde (100.0 g, 246 mmol, 1 eq), morpholine (50 mL, 492 mmol, 2 eq) in $CH_2Cl_2$ (1.0 L) and Methanol (500 mL) was added sodium triacetoxyborohydride (104 g, 492 mmol, 2 eq) under $N_2$ atmosphere. The reaction mixture was stirred at room temperature for 3 hours. After completion of the reaction by LC/MS, the mixture was neutralized by addition of an aqueous saturated solution of $NaHCO_3$ and extracted with $CH_2Cl_2$ (2×5.0 L). The combined organic extracts were washed with brine (2.0 L), dried over sodium sulfate, filtered and concentrated under vacuum to afford a thick brown solid. The resulting crude brown solid was purified by chromatography on silica gel to afford 73.0 g of the title compound as a yellow solid.

Yield: 63%.

HPLC: 95.97% (254 nm).

LC/MS: Mass found (m/z, M+1, 478.3), Area 96.62%.

$^1$H NMR (DMSO-$d_6$, 400 MHz) δ 9.24 (s, 1H), 8.74 (s, 1H), 8.03 (d, J 5.4 Hz, 1H), 7.76 (s, 1H), 7.70 (d, J 5.4 Hz, 1H), 7.59 (m, 1H), 7.39 (m, 2H), 3.56 (m, 4H), 2.65 (m, 2H), 2.28 (m, 6H), 1.73 (m, 2H), 1.36 (s, 9H).

Step 7: 6-(3-Morpholin-4-yl-propyl)-2-(thieno[3,2-c]pyridin-6-yl)-4H-chromen-4-one oxime

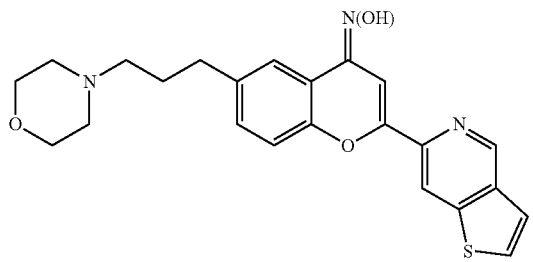

To a stirred solution of 6-(3-morpholin-4-yl-propyl)-2-(thieno[3,2-c]pyridin-6-yl)-4H-chromen-4-one O-tert-butyl oxime (10.0 g, 21 mmol, 1 eq) in acetic acid (100 mL) was added a solution of dioxane-HCl (4 M, 150 mL, 3 eq) at room temperature under inert atmosphere. The reaction mixture was heated at 80° C. for 14 hours (LC/MS monitoring indicated 100% conversion). The organic solvents were concentrated under vacuum where a solid mass started to precipitate. The yellow solid was filtered off, washed with dioxane (200 mL), $Et_2O$ (2×50 mL) to afford 8 g of a yellow solid as a HCl salt.

Yield: 90%

HPLC purity: 98.44% (254 nm). E/Z ratio=97.54%/1.75%.

LC/MS: Mass found (m/z, M+, 422.3), Area 97.3%.

$^1$H NMR (DMSO, 400 MHz) δ 11.06 (brs, 1H), 10.72 (brs, 1H), 9.28 (s, 1H), 8.80 (s, 1H), 8.07 (d, J 5.4 Hz, 1H), 7.76-7.70 (m, 3H), 7.47-7.41 (m, 2H), 3.95 (m, 2H), 3.80 (m, 2H), 3.42, (m, 2H), 3.08 (m, 4H), 2.71 (m, 2H), 2.10 (m, 2H).

Example 2: Biological Evaluation of the Compound of Formula (I)

The compound of formula (I) according to the invention (i.e., PXT002331) was tested for its agonistic and/or positive allosteric modulator activity on human mGluR4 using the calcium assay described in Example 171 of WO 2011/051478. PXT002331 was found to have a potency of $pEC_{50}$=7.12 (corresponding to an $EC_{50}$ of about 0.076 µM), which is comparable to that of the compound of Example 127 of WO 2011/051478 (i.e., "PXT001858") which has a $pEC_{50}$ of 7.44 (corresponding to an $EC_{50}$ of about 0.036 µM).

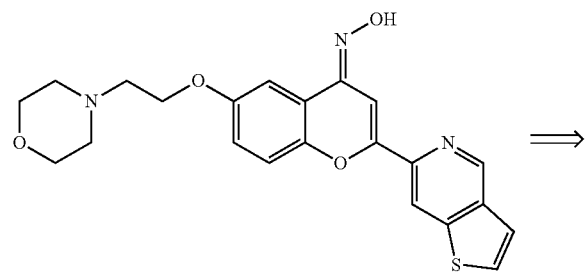

PXT001858
pEC50 = 7.44
cLogP 4.18
PSA 105

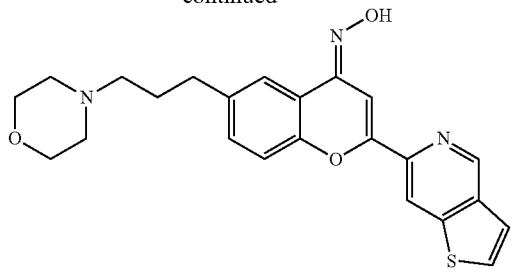

PXT002331
pEC50 = 7.12
cLogP 4.91
PSA 95

The in vitro ADME profile of PXT002331 was also very similar with reference to phase I metabolic stability: CL (h/r): 55/101 μl/min/mg protein and intestinal absorption: CaCo-2 (A-B, pgp): 4.11. 10-6 cm/s, no efflux.

In both cases, i.e. PXT002331 and PXT001858, plasma protein binding was high with less than 1% of free fraction and compounds do not suffer from a lack of solubility (s>10 mg/ml in water) as hydrochloride salt.

However, despite very similar physico-chemical properties and ADME profiles, PXT002331 was found to show an unexpected, highly advantageous oral in vivo PK profile when compared to PXT001858, as described in the following.

In Vivo Pharmacokinetics Evaluation:

PXT002331 and PXT001858 were administered per os (p.o.) at 10 mg/kg to male Sprague-Dawley rats. Volume of administration was 10 ml/kg. In parallel, PXT002331 was also administered intravenously (i.v.) at 1 mg/kg, with a volume of administration of 2 ml/kg. Blood samples (200 μl) were collected at time ranging from 15 minutes to 24 hours for the p.o. administration and from 5 minutes to 24 hours for the i.v. administration in ice-cold tubes containing 0.2% K$_2$EDTA. Tubes were centrifuged at 10,000 rpm for 5 minutes at 4° C. The plasma (supernatant) was separated in another tube and stored at −80° C. until analysis. Two groups of 3 animals were used for each route of administration: in one group, blood samples were collected to determine the kinetics of plasma exposure over a 24-hour period, and in the second group, blood and brain were collected at one terminal time point (0.5, 1.0, 1.5, 2.0, 4.0 hours) to determine the kinetics of brain exposure and brain/plasma ratio.

Compound Analysis:

The respective parent compound (free base) was analysed in plasma samples and in brain homogenate using a LC-MS/MS method. Concentrations are expressed in ng/ml of plasma or in ng/g of brain tissue.

Results:

At 10 mg/kg, using the same vehicle (Tween-80/Ethanol/30% HPBCD (2/10/88)), PXT002331 showed a comparable plasma exposure than PXT001858 as reflected by its AUC (1.1-fold) and Cmax (0.7-fold). Oral bioavailability of PXT002331 in this experiment was 39%. Despite their similar oral absorption, PXT002331 has a higher brain/plasma ratio (6.5 versus 2.0 at T=1.5 h; see FIG. 4) leading to a 3-fold improvement in the brain AUC when compared to PXT001858. A. posteriori, one potential hypothesis might rely on the difference of phase II conjugation in the intestine and liver during oral absorption. When both compounds were assayed in vitro in the presence of UGT (UDP-Glucuronosyl transferase), PXT002331 showed a much lower level of glucuronidation as compared to PXT001858 (see table below). Nonetheless, this difference observed in vitro cannot by itself explain the unexpected advantageous PK results obtained with PXT002331. The results obtained in these experiments are furthermore summarized in Tables 1 to 3 below and in FIGS. 1 to 4.

TABLE 1

PK parameters of PXT002331 and PXT001858 after oral administration in rats at 10 mg/kg.

| Oral PK 10 mpk | Brain/Plasma ratio (T = 1.5 h) | Cmax (Brain) (ng/G tissue) | Plasma AUC inf(h * ng/ml) | Brain AUC inf(h * ng/g) |
|---|---|---|---|---|
| PXT002331 | 6.5 | 818 | 432 | 2713 |
| PXT001858 | 2.0 | 521 | 394 | 838 |

TABLE 2

PXT002331 and PXT001858 in vitro glucuronidation (peak area) in rat liver microsomes.

| | Time (min) | | | | |
|---|---|---|---|---|---|
| | 0 | 5 | 15 | 30 | 60 |
| PXT002331 | 0 | 0 | 0 | 0 | 0 |
| PXT001858 | 0 | 164 | 353 | 798 | 2 556 |

TABLE 3

PXT002331 and PXT001858 in vitro glucuronidation (peak area) in rat intestinal microsomes.

| | Time (min) | | | | |
|---|---|---|---|---|---|
| | 0 | 5 | 15 | 30 | 60 |
| PXT002331 | 0 | 2 492 | 4 724 | 8 369 | 16 897 |
| PXT001858 | 0 | 13 840 | 30 396 | 68 072 | 14 8307 |

These results demonstrate that the compound of formula (I) according to the present invention i.e. PXT002331, has highly advantageous pharmacokinetic properties and shows a considerably improved brain exposure as compared to the compound of Example 127 of WO2011/051478 ("PXT001858"). These properties render the compound of formula (I) particularly suitable as a therapeutic agent, e.g., for the treatment or prevention of neurological and/or psychiatric disorders.

Example 3: In Vivo Evaluation of the Compound of Formula (I) in an MPTP Monkey Model of Parkinson's Disease The anti-parkinsonian efficacy of the compound of formula (I) according to the present invention (i.e., PXT002331) was evaluated in the 1-methyl-4-phenyl-1,2,3,6-tetrahydropyridine (MPTP) macaque model of Parkinson's disease (using macaques of the species Macaca fascicularis), which reproduces most of the clinical and pathological hallmarks of Parkinson's disease and is considered a "gold standard" (see Porras G et al., Cold Spring Harb Perspect Med., 2(3):a009308, 2012 and references cited therein for a general description of the MPTP model).

The results of these studies are summarized in FIGS. 5A to 5F. In particular, it was found that PXT002331 as a stand-alone treatment shows potent anti-parkinsonian activity in MPTP-treated macaques, with an optimal improvement of the parkinsonian score at administration doses of 2 to 25 mg/kg perorally (p.o.) twice a day (see FIG. 5A). In this experiment, PXT002331 was orally administered twice a day during a period of 4 days, and the parkinsonian score was assessed at day 4 over 2 hours of observation (data are mean values+standard error of the mean (s.e.m.); n=7 monkeys per group).

Figure 5A:
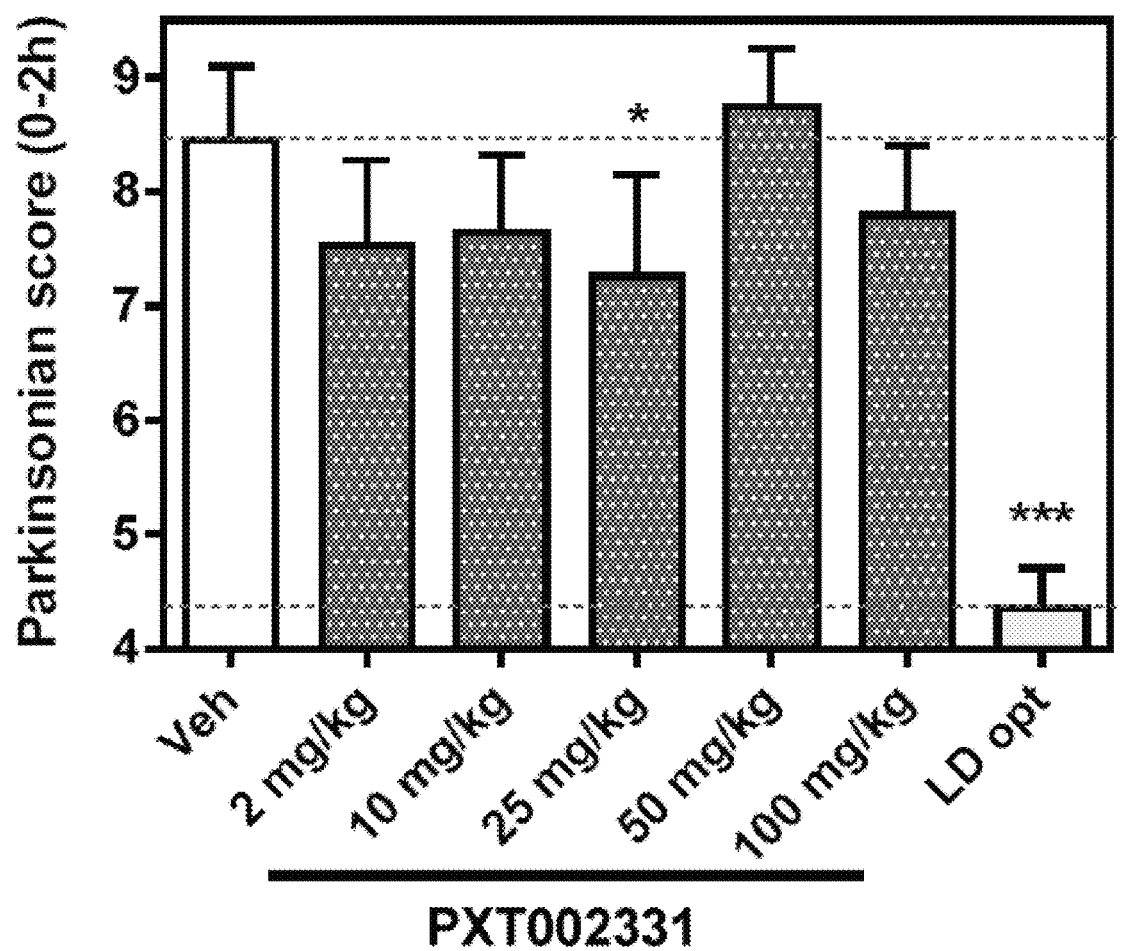
Figure 5B:
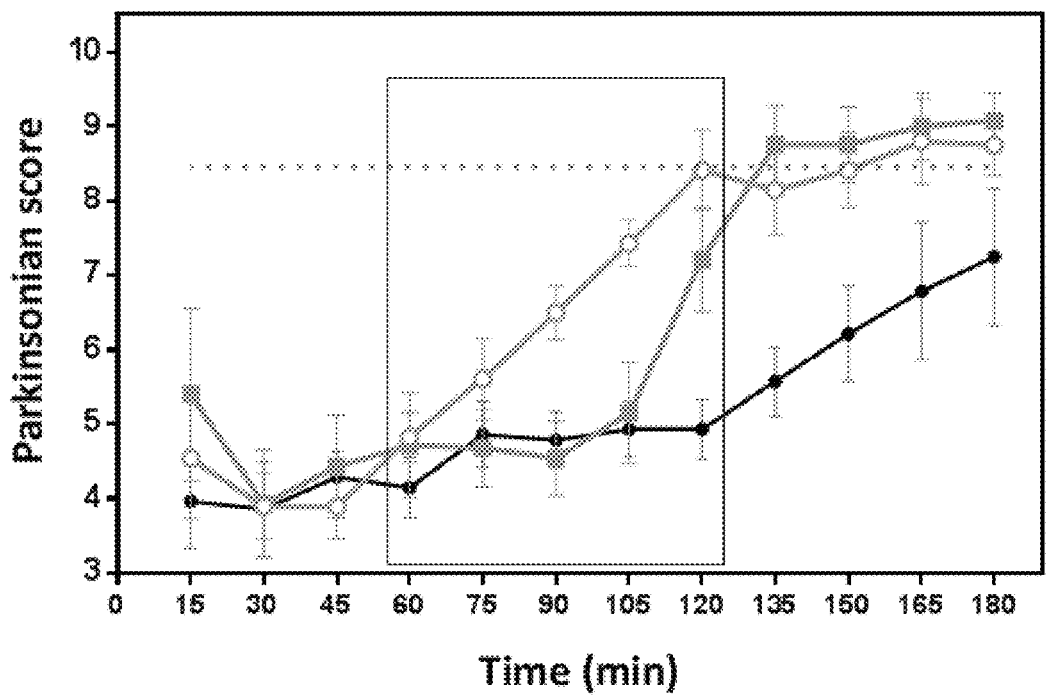
Figure 5C:
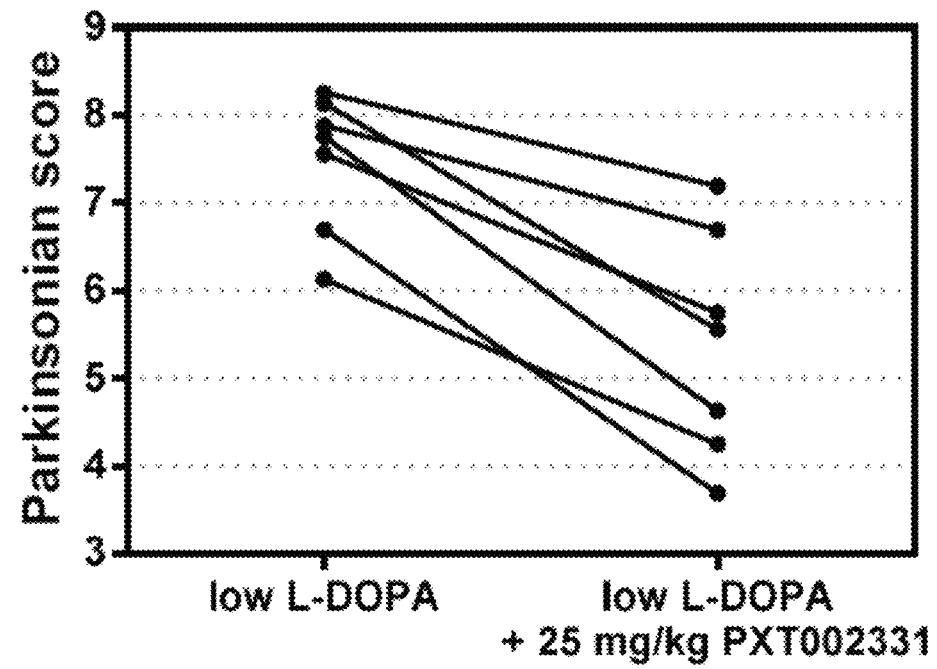
Figure 5C:
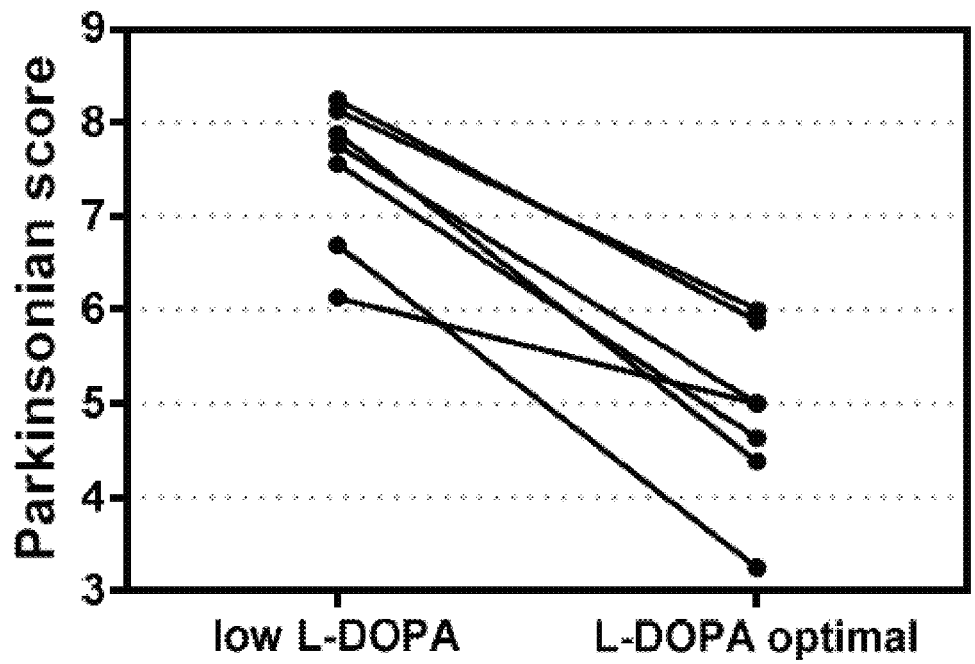

The anti-parkinsonian efficacy of PXT002331 (25 mg/kg) was further evaluated in combination with low (suboptimal) doses of L-dopa (levodopa; 4-9 mg/kg) (see FIGS. 5B and 5C). Doses were orally administered twice a day during 4 days, and assessment of parkinsonian scores took place at day 4 (between 1 and 2 h after L-dopa administration, i.e., between 2 and 3 h after PXT002331 administration). As also shown in FIG. 5B, it was found that the combined administration of PXT002331 and a suboptimal dose of L-dopa gave a considerable improvement in parkinsonian score as compared to the administration of L-dopa (suboptimal dose) alone. These data furthermore point to an increase of the "on"-time achieved by PXT002331 in combination with L-dopa, which is a clinically highly relevant advantage, as also reflected by the fact that "on"-time is an endpoint for the assessment of clinical efficacy in phase 3 in Parkinson's disease patients. Remarkably, all treated monkeys showed a significant improvement in parkinsonian score, which indicates a high robustness of the anti-parkinsonian effect of PXT002331 (see FIG. 5C). These results confirm that PXT002331 can advantageously be used as an add-on treatment together with L-dopa (levodopa).

Figure 5D:
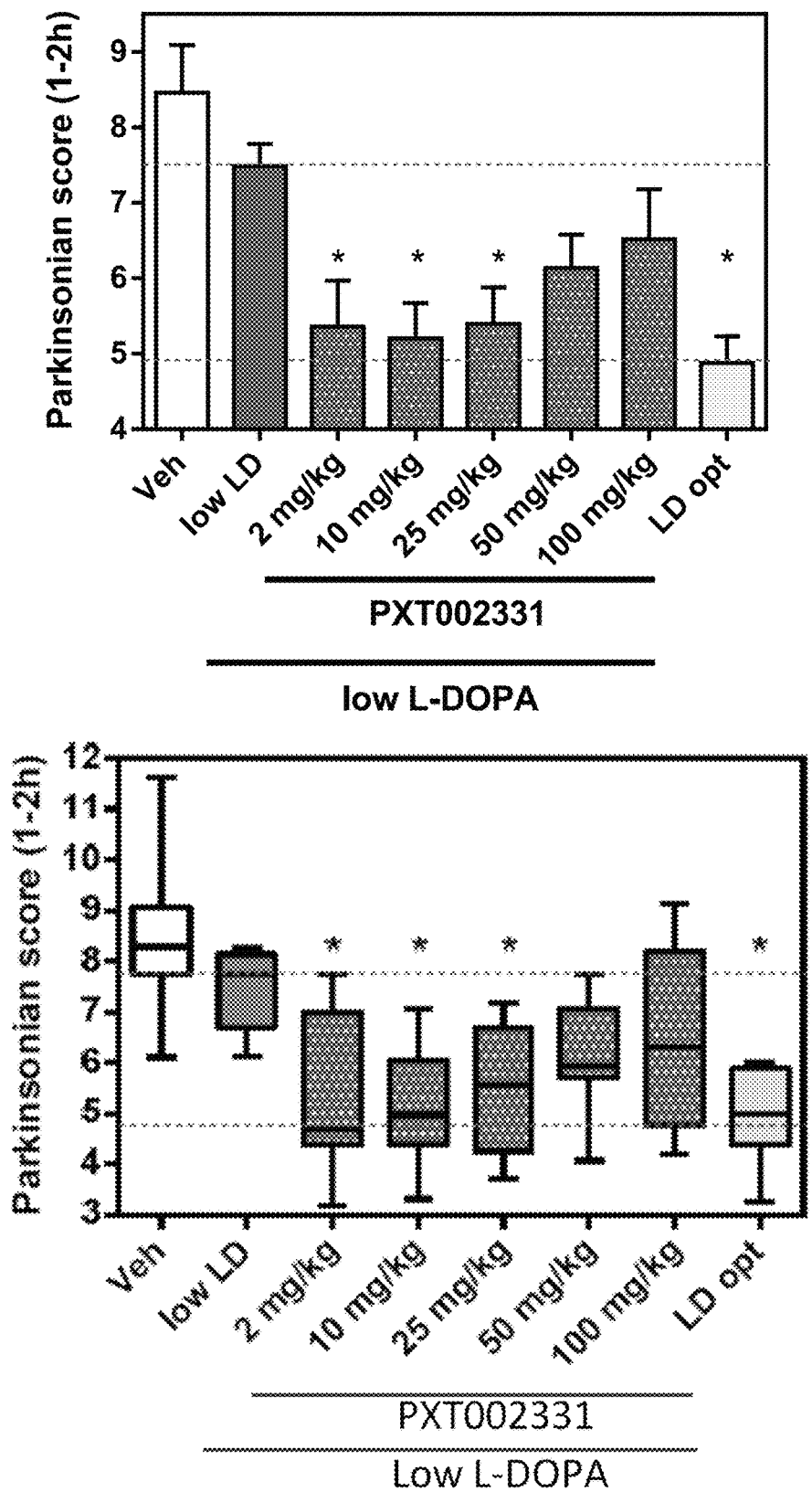

The results of a dose-response evaluation of the combination of PXT002331 (at doses from 2 mg/kg to 100 mg/kg) with L-dopa (low dose) are shown in FIG. 5D (the assessment of parkinsonian scores took place at day 4). It was found that PXT002331 in combination with L-dopa provides a highly potent anti-parkinsonian effect upon oral administration over a range of different doses. The optimal anti-parkinsonian efficacy was achieved with administration doses of PXT002331 of 2 mg/kg to 25 mg/kg.

Figure 5E:
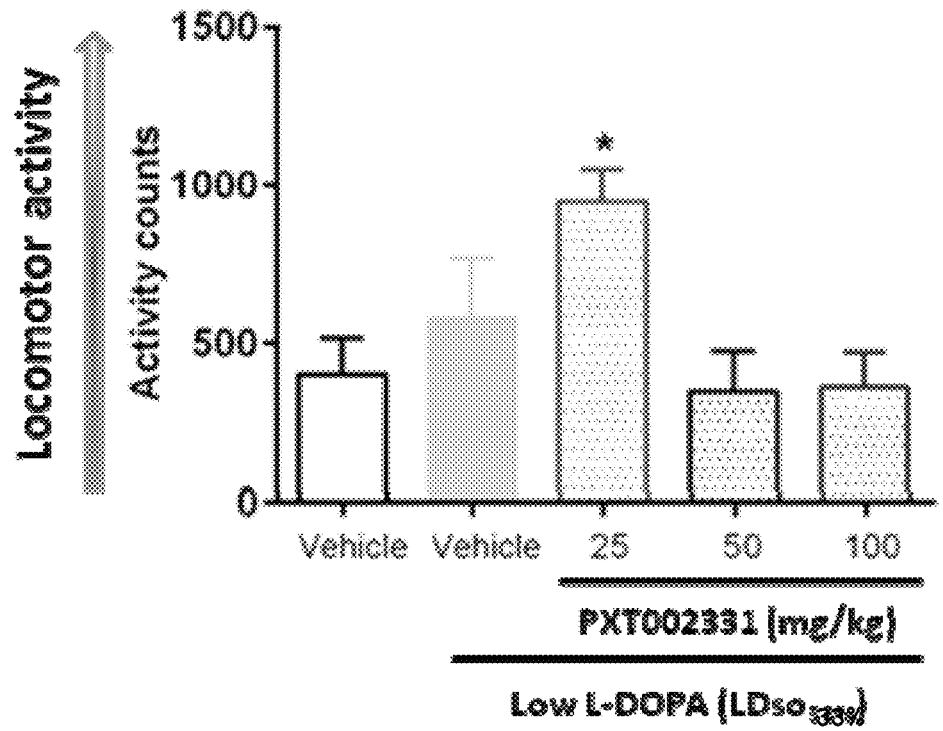
Figure 5E:
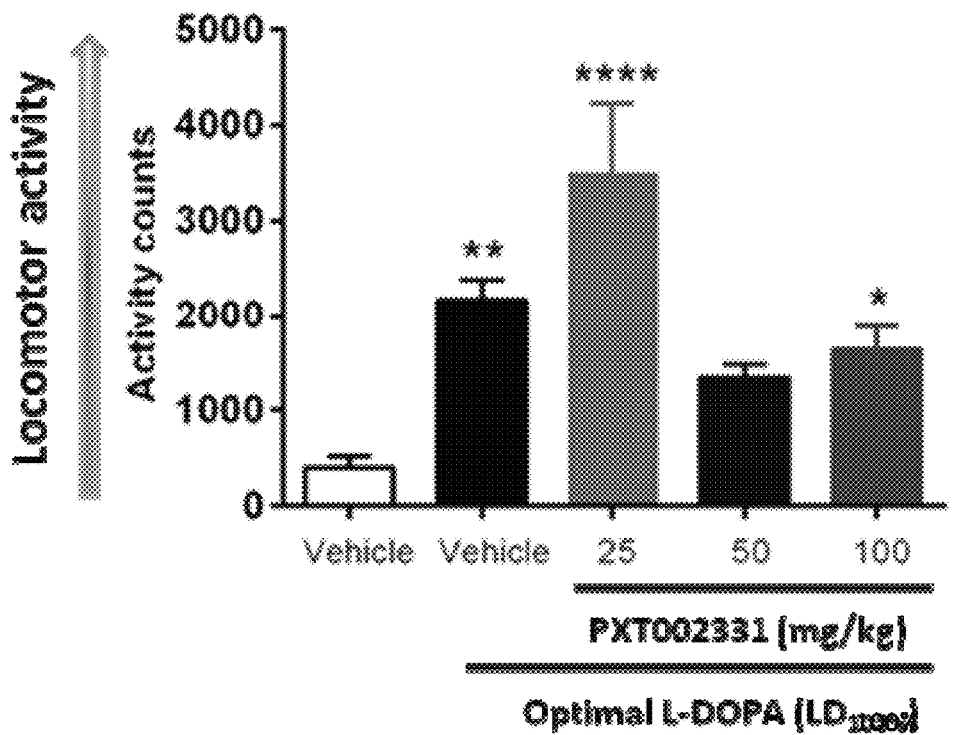

A significant improvement in locomotor activity could further be demonstrated for PXT002331 (25 mg/kg) administered orally in combination with either a low dose of L-dopa or an optimal dose of L-dopa, as also shown in FIG. 5E (early stage PD monkey model; N=5). In this experiment, each monkey was equipped with a detector of movements and signals were collected with 24 light beams and a video track recorder in order to descriminate all types of movements. The locomotor activity was measured during 1 hour.

Figure 5F:
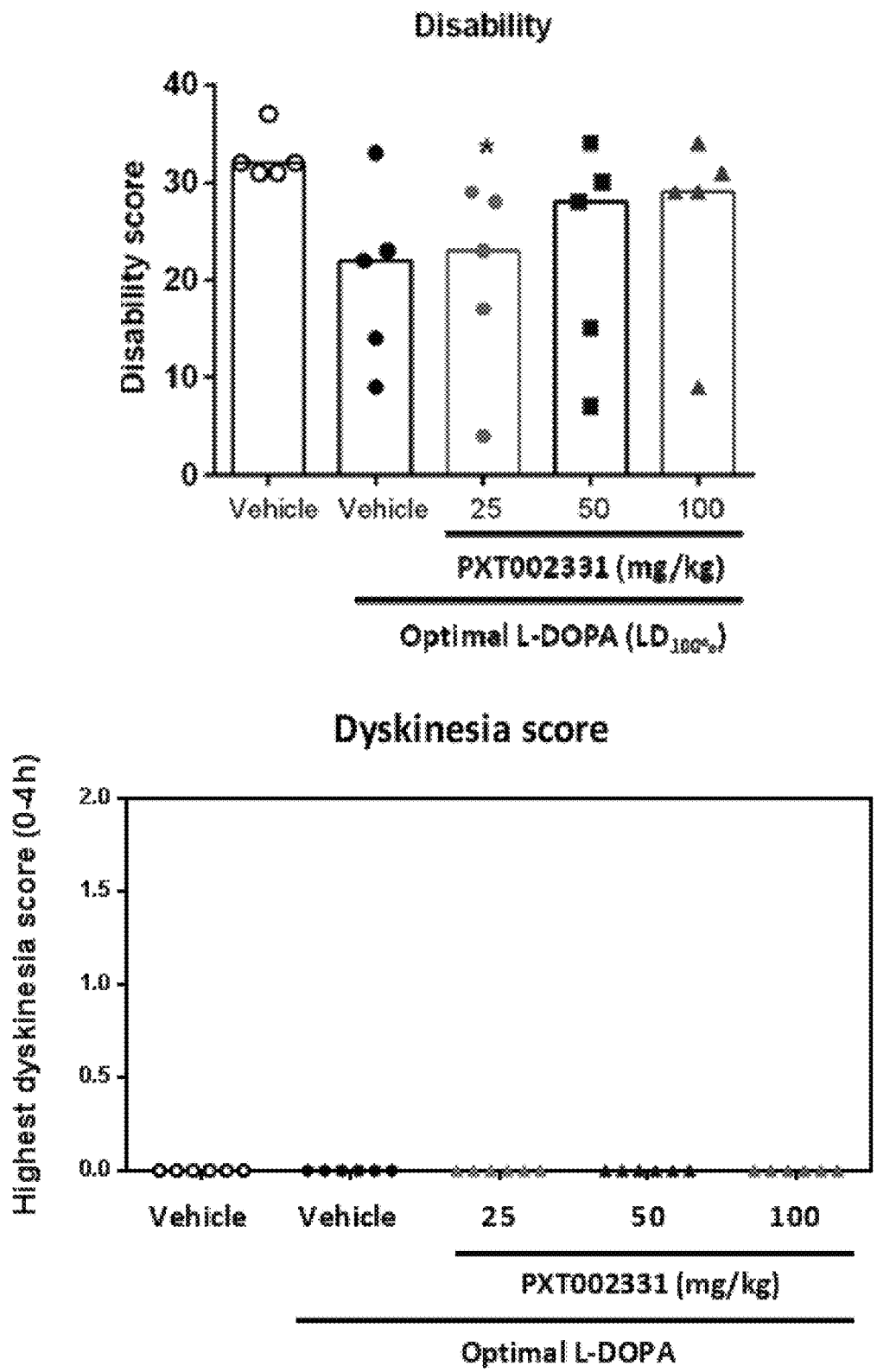

As shown in FIG. 5F, it was furthermore found that increasing doses of PXT002331 in combination with L-dopa (optimal dose) provided an improvement in the disability score, without inducing dyskinesia. A particularly advantageous improvement in the disability score could be achieved using 25 mg/kg PXT002331 in combination with L-dopa (optimal dose). Moreover, none of the tested combinations of PXT002331 (at doses from 25 mg/kg to 100 mg/kg) with an optimal (high) dose of L-dopa resulted in any induction of dyskinesia, which is an undesirable adverse effect that typically occurs during treatment with L-dopa.

These findings confirm that PXT002331 is highly advantageous for use in the treatment or prevention of Parkinson's disease, both in monotherapy (without the concomitant use of further antiparkinson drugs) and in cotherapy using further antiparkinson drugs such as L-dopa (levodopa). In these experiments, doses of 2 mg/kg to 25 mg/kg of PXT002331, to be orally administered twice per day, were found to be particularly efficacious.

The invention claimed is:

1. A compound of the following formula (I):

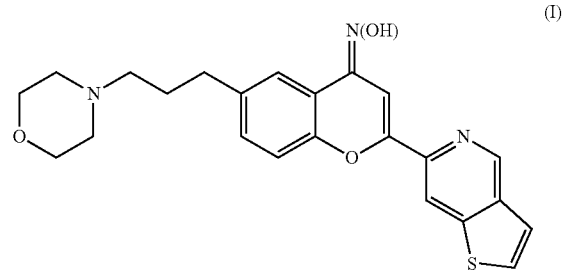

or a pharmaceutically acceptable salt thereof.

2. The compound of claim 1, wherein said compound or pharmaceutically acceptable salt thereof has the (E)-configuration at the oxime group comprised in formula (I).

3. The compound of claim 1, wherein the pharmaceutically acceptable salt is a hydrochloride salt.

4. The compound of claim 2, wherein the pharmaceutically acceptable salt is a hydrochloride salt.

5. A pharmaceutical composition comprising the compound or pharmaceutically acceptable salt thereof of claim 1 and a pharmaceutically acceptable excipient.

* * * * *